(12) United States Patent
Kanada

(10) Patent No.: US 10,559,379 B2
(45) Date of Patent: Feb. 11, 2020

(54) DIAGNOSIS SUPPORT APPARATUS, OPERATION METHOD FOR THE SAME, AND DIAGNOSIS SUPPORT SYSTEM

(71) Applicant: FUJIFILM Corporation, Tokyo (JP)

(72) Inventor: Shoji Kanada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 228 days.

(21) Appl. No.: 15/834,895

(22) Filed: Dec. 7, 2017

(65) Prior Publication Data

US 2018/0166167 A1 Jun. 14, 2018

(30) Foreign Application Priority Data

Dec. 9, 2016 (JP) .................................. 2016-239377

(51) Int. Cl.
*G06K 9/00* (2006.01)
*G16H 30/40* (2018.01)
(Continued)

(52) U.S. Cl.
CPC ........... *G16H 30/40* (2018.01); *A61B 5/0035* (2013.01); *G06T 7/0012* (2013.01); *G16H 10/60* (2018.01);
(Continued)

(58) Field of Classification Search
CPC . A61B 5/0033; A61B 5/02007; A61B 5/7264; A61B 5/742; G06T 7/00; G06T 7/0002; G06T 7/0012; G06T 7/12; G06T 7/11; G06T 7/174; G06T 1/00; G06T 7/0016; G06T 7/0085; G06T 7/60; G06T 2207/10116; G06T 2207/30004; G06T 5/40; G06T 2207/30068; G06T 7/0083; G06T 7/0081; G16H 30/00; G16H 30/20; G16H 30/40; G16H 30/60; G01N 33/4833; G01N 33/48; G01N 33/5091;
(Continued)

(56) References Cited

U.S. PATENT DOCUMENTS

| 5,779,634 A | 7/1998 | Ema et al. |
| 2016/0055394 A1 | 2/2016 | Kanada |
| 2017/0011199 A1* | 1/2017 | Oosawa .................. A61B 6/00 |

FOREIGN PATENT DOCUMENTS

| JP | 2015-191285 A | 11/2015 |
| JP | 3085724 B2 | 11/2015 |
| JP | 2016-045662 A | 4/2016 |

* cited by examiner

*Primary Examiner* — Duy M Dang
(74) *Attorney, Agent, or Firm* — Birch, Stewart, Kolasch & Birch, LLP

(57) ABSTRACT

A second image analysis portion performs image analysis on a target image so as to extract an extracted lesion which is a lesion present in the target image, specifies the type thereof, and outputs an extraction result to a comparison portion. An information management portion reads a registered lesion corresponding to a disease name specified by a doctor from registered lesion information, and outputs the registered lesion to the comparison portion. The comparison portion compares the type of extracted lesion with the type of registered lesion, and outputs a comparison result to a screen output control portion. The screen output control portion outputs information display screen including reliability information indicating the reliability of the disease name specified by the doctor on the basis of a comparison result.

10 Claims, 35 Drawing Sheets

(51) Int. Cl.
    *A61B 5/00*          (2006.01)
    *G16H 30/20*       (2018.01)
    *G06T 7/00*         (2017.01)
    *G16H 10/60*       (2018.01)
    *G16H 70/60*       (2018.01)

(52) U.S. Cl.
    CPC ... *G16H 30/20* (2018.01); *G06T 2207/30096* (2013.01); *G16H 70/60* (2018.01)

(58) Field of Classification Search
    CPC ...... G06K 9/4604; G06K 9/52; G06K 9/6267; G06K 9/66; G06F 19/321
    See application file for complete search history.

| CASE ID | CASE IMAGE | CASE LESION INFORMATION ||| IMAGE READING REPORT INFORMATION |||
|---|---|---|---|---|---|---|---|
| | | LESION ID | TYPE | FEATURE AMOUNT | REPORT ID | FINDINGS | DISEASE NAME |
| C001 | F001-1 TO 20 (20C) | L001 | FROSTED GLASSY SHADOW | ZC11, ZC21, ZC31,··· | R001 | FROSTED GLASSY SHADOW IN LEFT MIDDLE LOBE··· | BACTERIAL PNEUMONIA |
| | | L002 | INFILTRATIVE SHADOW | ZC12, ZC22, ZC32,··· | | | |
| | | ··· | | ··· | | | |

| DISEASE NAME | REGISTERED LESION |
|---|---|
| BACTERIAL PNEUMONIA | FROSTED GLASSY SHADOW |
| | INFILTRATIVE SHADOW |
| TUBERCULOSIS | CENTRILOBULAR NODULE SHADOW |
| | TUMOR SHADOW |
| | CAVITY |
| | INFILTRATIVE SHADOW |
| INTERSTITIAL PNEUMONIA | FROSTED GLASSY SHADOW |
| | RETICULAR SHADOW |
| | HONEYCOMB LUNG |
| | TRACTION BRONCHODILATION |
| | INFILTRATIVE SHADOW |
| ⋮ | ⋮ |

FIG. 35

| DISEASE N10 | | 115 |
| --- | --- |
| SEVERITY | LESION |
| 1 | A |
| 2 | Aa, B |
| 3 | Aaa, Bb, C |
| 4 | Aaaa, Bbb, Cc, D |

SLIGHT CASE ↑

↓ SERIOUS CASE

FIG. 38

| DISEASE NAME | REGISTERED LESION | OCCURRENCE FREQUENCY (%) |
|---|---|---|
| BACTERIAL PNEUMONIA | FROSTED GLASSY SHADOW | 100 |
| | INFILTRATIVE SHADOW | 80 |
| TUBERCULOSIS | CENTRILOBULAR NODULE SHADOW | 90 |
| | TUMOR SHADOW | 70 |
| | CAVITY | 35 |
| | INFILTRATIVE SHADOW | 20 |
| INTERSTITIAL PNEUMONIA | FROSTED GLASSY SHADOW | 90 |
| | RETICULAR SHADOW | 70 |
| | HONEYCOMB LUNG | 55 |
| | TRACTION BRONCHODILATION | 80 |
| | INFILTRATIVE SHADOW | 35 |
| ⋮ | ⋮ | ⋮ |

DIAGNOSIS SUPPORT APPARATUS, OPERATION METHOD FOR THE SAME, AND DIAGNOSIS SUPPORT SYSTEM

CROSS-REFERENCE TO RELATED APPLICATION

This application claims priority under 35 USC 119 from Japanese Patent Application No. 2016-239377, filed 9 Dec. 2016, the disclosure of which is incorporated by reference herein.

BACKGROUND OF THE INVENTION

1. Field of the Invention

The present invention relates to a diagnosis support apparatus, an operation method for the diagnosis support apparatus, and a diagnosis support system.

2. Description of the Related Art

In the related art, in a medical site, a doctor reads an examination image captured by a modality such as an X-ray computed tomography (CT), and creates an image reading report in which a result thereof is summarized. The result described in the image reading report includes findings such as a position, a size, and the type of lesion (a frosted glassy shadow, an infiltrative shadow, emphysema, or the like) present in the examination image, and a disease name. In a case where an image reading report is created, a diagnosis support apparatus using a computed-aided diagnosis (CAD) technique is frequency used in order to reduce work time and a burden on a doctor (for example, refer to JP3085724B (corresponding to U.S. Pat. No. 5,779,634A)).

A diagnosis support apparatus disclosed in JP3085724B performs image analysis on an image reading target examination image (hereinafter, referred to as a target image) so as to extract a plurality of types of lesions (hereinafter, referred to as a target lesion) such as a shadow of an interstitial disease and a shadow of a nodule. The extracted target lesion (hereinafter, referred to as an extracted lesion) is compared with a lesion (hereinafter, referred to as a visually recognized lesion) which is visually recognized by a doctor and for which findings are described in an image reading report. As a result of the comparison, in a case where there is a lesion which is not included in the visually recognized lesion but included in the extracted lesion, that is, a lesion which is overlooked (hereinafter, referred to as, an overlooked lesion) by the doctor, a sound or a message indicating that there is the overlooked lesion is issued or displayed to the doctor for warning.

The type of lesion and a disease have a correspondence relationship. For example, in a case where there are two types of lesions such as a frosted glassy shadow and an infiltrative shadow, bacterial pneumonia is considered as a disease. Thus, a doctor specifies a disease name on the basis of the type of visually recognized lesion, and the medical knowledge or experience cultivated until then. In a case where there is an overlooked lesion at this time, according to the diagnosis support apparatus disclosed in Japanese Patent No. 3085724, the fact is displayed for warning. Therefore, the doctor has a chance to correct the disease name temporarily specified on the basis of the visually recognized lesion to a disease name in which the overlooked lesion is referred to.

However, in the diagnosis support apparatus disclosed in Japanese Patent No. 3085724, even if the doctor has a chance to correct a disease name through warning display of the overlooked lesion, there may be a case where correction to a disease name in which an overlooked lesion is referred to is not performed due to various factors such as a lack of knowledge of the doctor, a lack of experience, or a careless mistake despite warning display of the overlooked lesion. That is to say, even if overlooking of a lesion is noticed, it is not finally clear whether or not a doctor accurately specifies a disease name by referring to all lesions. In other words, the diagnosis support apparatus disclosed in Japanese Patent No. 3085724 supports removal of an overlooked lesion, but does not directly support an image reading process of a doctor of specifying a disease name on the basis of the type of lesion. Thus, the reliability of a disease name specified by a doctor is not ensured.

SUMMARY OF THE INVENTION

An object of the present invention is to provide a diagnosis support apparatus, an operation method for the diagnosis support apparatus, and a diagnosis support system, capable of ensuring the reliability of a disease name specified by a doctor.

In order to solve the above-described problem, according to the present invention, there is provided a diagnosis support apparatus comprising a reception unit that receives entry of a disease name specified by a doctor visually recognizing a target image which is an examination image of a certain patient and is an image reading target of the doctor; a type acquisition unit that acquires the type of extracted lesion which is a lesion present in the target image and is extracted by performing image analysis on the target image; an information management unit that manages registered lesion information in which the disease name and a registered lesion corresponding to the disease name are registered, and reads the registered lesion corresponding to the disease name received by the reception unit; a comparison unit that compares the type of registered lesion read by the information management unit with the type of extracted lesion acquired by the type acquisition unit; and an output control unit that outputs reliability information regarding the reliability of the disease name received by the reception unit on the basis of a comparison result in the comparison unit.

Preferably, in a case where there is a non-reference lesion which is a type of lesion included in the extracted lesion and not included in the registered lesion, the output control unit outputs a warning indicating that the non-reference lesion is not referred to in specifying the disease name as the reliability information.

The diagnosis support apparatus preferably further comprises a similar case acquisition unit that acquires similar cases from a similar case search apparatus which searches for the similar cases including a case image similar to the target image among a plurality of cases including the case image which is the examination image obtained in the past.

Preferably, the case includes the disease name, the similar case acquisition unit outputs the similar cases to the output control unit, the output control unit outputs a similar case selection screen for receiving selection of one of the similar cases, and the reception unit receives the disease name included in the similar case selected on the similar case selection screen as the disease name specified by the doctor.

Preferably, the case includes the disease name and the type of case lesion which is a lesion presented in the case image, the similar case acquisition unit outputs the similar cases to the information management unit, the information management unit updates the registered lesion information on the basis of the disease name included in the similar case from similar case acquisition unit and the type of case lesion, and the comparison unit compares the type of registered lesion read by the information management unit from the registered lesion information after being updated with the type of extracted lesion acquired from the type acquisition unit.

Preferably, an occurrence frequency of the registered lesion is registered in the registered lesion information for each disease name, and the output control unit makes output aspects of the reliability information different from each other depending on the occurrence frequency of a non-reference lesion which is a type of lesion included in the extracted lesion and not included in the registered lesion.

Preferably, the output control unit outputs an information display screen on which the reliability information is displayed, and the information display screen is provided with a link for displaying the target image in which a non-reference lesion which is a type of lesion included in the extracted lesion and not included in the registered lesion is present.

Preferably, the output control unit outputs an image display screen on which the target image including the non-reference lesion is displayed in response to selection of the link, and the non-reference lesion and other lesions are displayed in different aspects on the image display screen.

According to the present invention, there is provided an operation method for a diagnosis support apparatus, comprising a reception step of receiving entry of a disease name specified by a doctor visually recognizing a target image which is an examination image of a certain patient and is an image reading target of the doctor; a type acquisition step of acquiring the type of extracted lesion which is a lesion present in the target image and is extracted by performing image analysis on the target image; an information management step of managing registered lesion information in which the disease name and a registered lesion corresponding to the disease name are registered, and reads the registered lesion corresponding to the disease name received in the reception step; a comparison step of comparing the type of registered lesion read in the information management step with the type of extracted lesion acquired in the type acquisition step; and an output control step of outputting reliability information regarding the reliability of the disease name received in the reception step on the basis of a comparison result in the comparison step.

According to the present invention, there is provided a diagnosis support system comprising a diagnosis support apparatus supporting a doctor's diagnosis and a client terminal connected to the diagnosis support apparatus via a network and operated by the doctor, the system including a reception unit that receives entry of a disease name specified by the doctor visually recognizing a target image which is an examination image of a certain patient and is an image reading target of the doctor; a type acquisition unit that acquires the type of extracted lesion which is a lesion present in the target image and is extracted by performing image analysis on the target image; an information management unit that manages registered lesion information in which the disease name and a registered lesion corresponding to the disease name are registered, and reads the registered lesion corresponding to the disease name received by the reception unit; a comparison unit that compares the type of registered lesion read by the information management unit with the type of extracted lesion acquired by the type acquisition unit; and an output control unit that outputs reliability information regarding the reliability of the disease name received by the reception unit on the basis of a comparison result in the comparison unit.

According to the present invention, since information regarding the reliability of a disease name specified by a doctor is output on the basis of a comparison result between the type of extracted lesion which is a lesion present in a target image and is extracted by performing image analysis on the target image, and the type of registered lesion corresponding to the disease name specified by the doctor, it is possible to provide a diagnosis support apparatus, an operation method for the diagnosis support apparatus, and a diagnosis support system, capable of ensuring the reliability of the disease name specified by the doctor.

BRIEF DESCRIPTION OF THE DRAWINGS

FIG. 35 is a table illustrating a relationship between the severity and a lesion of a certain disease.

FIG. 38 is a diagram illustrating registered lesion information in which an occurrence frequency of a registered lesion is registered.

DESCRIPTION OF THE PREFERRED EMBODIMENTS

First Embodiment

Figure 1:
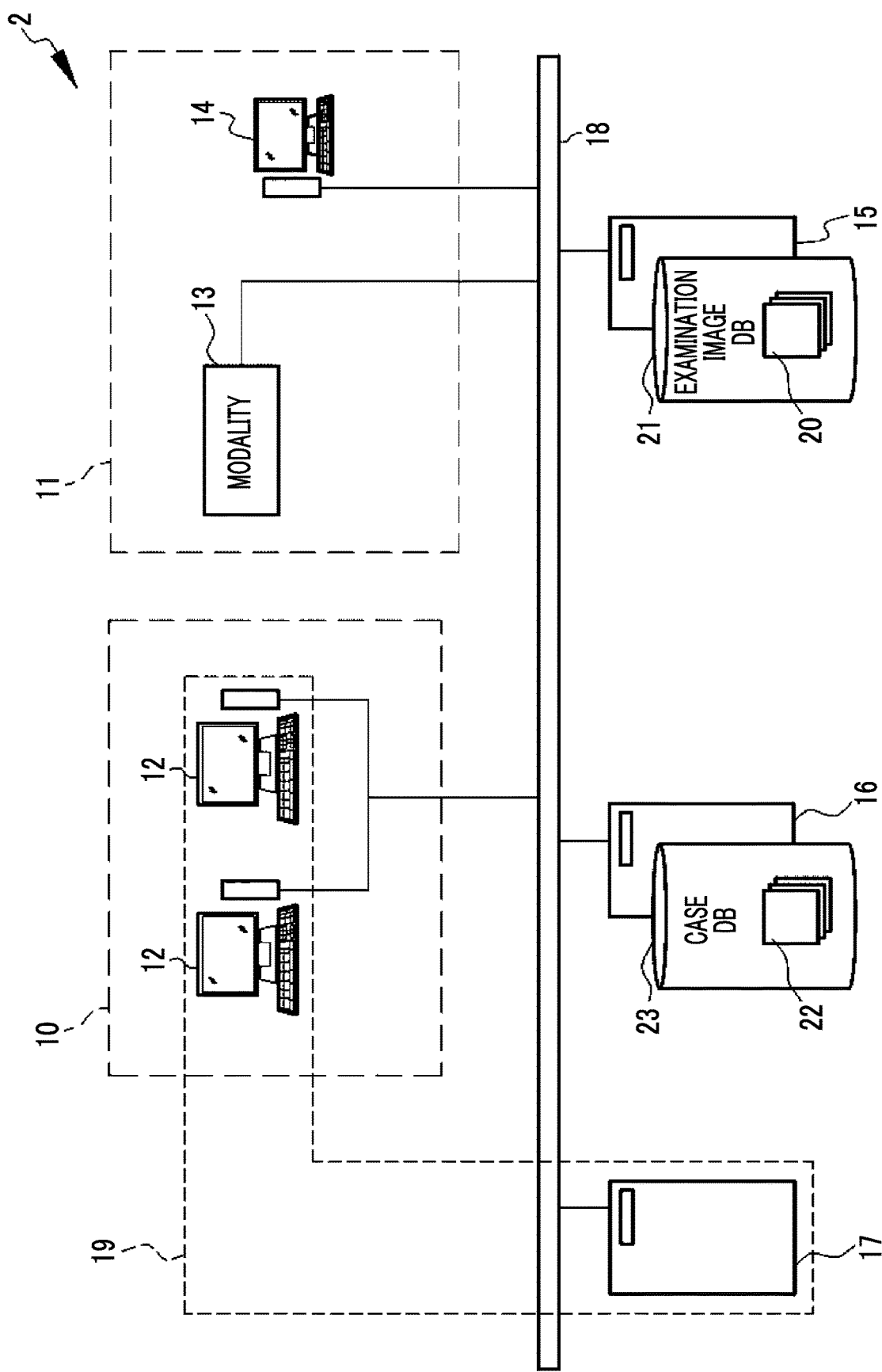
FIG. 1 is a diagram illustrating a medical information system including a diagnosis support server.

In FIG. 1, a medical information system 2 is built into a medical facility having a medical care department 10 and an examination department 11. The medical information system 2 corresponds to a client terminal, and is formed of medical care department terminals 12 provided in the medical care department 10; a modality 13 and an order management terminal 14 provided in the examination department 11; an examination image database (hereinafter, abbreviated to a DB) server 15; a case DB server 16; and a diagnosis support server 17 corresponding to a diagnosis support apparatus and a similar case search apparatus. These constituent elements are connected to each other via a network 18 such as a local area network (LAN) laid in the medical facility.

The medical care department terminals 12 form a diagnosis support system 19 along with the diagnosis support server 17. Each of the medical care department terminals 12 is used for a doctor DR (refer to FIG. 3) of the medical care department 10 not only to enter and view an electronic medical chart or an image reading report but also to issue an examination order for making a request for various medical examinations to the examination department 11. The medical care department terminal 12 is also used to view an examination image 20 captured by the modality 13, or a similar case and reliability information which will be described later, output from the diagnosis support server 17.

The modality 13 is, for example, a computed tomography (CT) apparatus or a magnetic resonance imaging (MRI) apparatus capturing a tomographic image as the examination image 20, or a simple X-ray imaging apparatus capturing a simple fluoroscopic image as the examination image 20. The order management terminal 14 receives an examination order issued by the medical care department terminal 12, and manages the received examination order. The examination order includes various items, for example, an order identification data (ID) for identifying each examination order, an ID of the medical care department terminal 12 or a doctor ID of the doctor DR issuing the examination order, a patient ID of an imaging target patient in the examination order, an examination purpose such as process observation, an imaging part such as the head or the chest, and an orientation such as facing up or facing down. A radiographer of the examination department 11 checks the content of the examination order on the order management terminal 14, sets imaging conditions corresponding to the checked examination order in the modality 13, and captures the examination image 20.

In a case where the examination image 20 is captured by the modality 13, information such as a patient ID of an imaging target patient and a radiographer ID of the radiographer performing imaging are entered by the radiographer. The entered information is correlated with the examination image 20 as accessory information.

The examination image 20 is created, for example, in a data file format based on the Digital Imaging and Communications in Medicine (DICOM) standard. A data file based on the DICOM standard is provided with a region in which data of the entity of the examination image 20 is stored, and is also provided with a region in which accessory information is stored. The accessory information includes patient information such as a patient ID, a patient name, the sex, the age, a height, and a weight of the patient, examination information such as an order ID, a doctor ID, the examination date and time, an examination purpose, an imaging part and orientation, imaging conditions, a radiographer ID, and the type of medical examination (the type of modality 13 such as CT or MRI), and an image ID for identifying each examination image 20. The image ID is automatically added by the modality 13 during capturing of the examination image 20. The modality 13 transmits the examination image 20 to the examination image DB server 15.

Regarding the examination image 20, only a single examination image may be captured as in a simple X-ray imaging apparatus with a single examination order, and a plurality of examination images may be captured as in a CT apparatus or an MRI apparatus. In the latter case, image IDs formed of a common number or symbol and serial numbers added to the plurality of examination images, and the plurality of examination images are treated as a set of examination images 20 captured with a single examination order.

The examination image DB server 15 is a so-called Picture Archiving and Communication System (PACS) server, and includes an examination image DB 21 in which a plurality of examination images 20 from the modality 13 are stored. The examination image DB server 15 transmits the examination image 20 to the medical care department terminal 12.

The case DB server 16 includes a case DB 23 in which a plurality of cases 22 are stored. The case DB server 16 transmits the cases 22 to the diagnosis support server 17.

Figure 2:
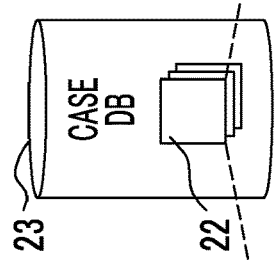
FIG. 2 is a diagram illustrating the content of cases.

In FIG. 2, each of the case 22 is added with a case ID for identifying each case 22 by the case DB server 16. The case 22 includes a case image 20C, case lesion information, and image reading report information. The case image 20C is the examination image 20 read in the past. FIG. 2 exemplifies the case image 20C in which twenty tomographic images with image IDs "F001-1 to F001-20" captured by a CT apparatus are treated as a set of images.

The case lesion information is information regarding a case lesion which is a lesion present in the case image 20C. The case lesion information includes a lesion ID for identifying each case lesion, the type of case lesion, and a feature amount ZC of the case lesion. FIG. 2 illustrates an example in which a frosted glassy shadow, an infiltrative shadow, and the like are registered as the types of case lesions.

The type of case lesion is one specified by a second image analysis portion 76 (refer to FIG. 11) of the diagnosis support server 17 during image reading in the past. The feature amount ZC of the case lesion is also one specified by a feature amount calculation portion 68 (refer to FIG. 10) of the diagnosis support server 17 during image reading in the past.

Figures 8, 9:
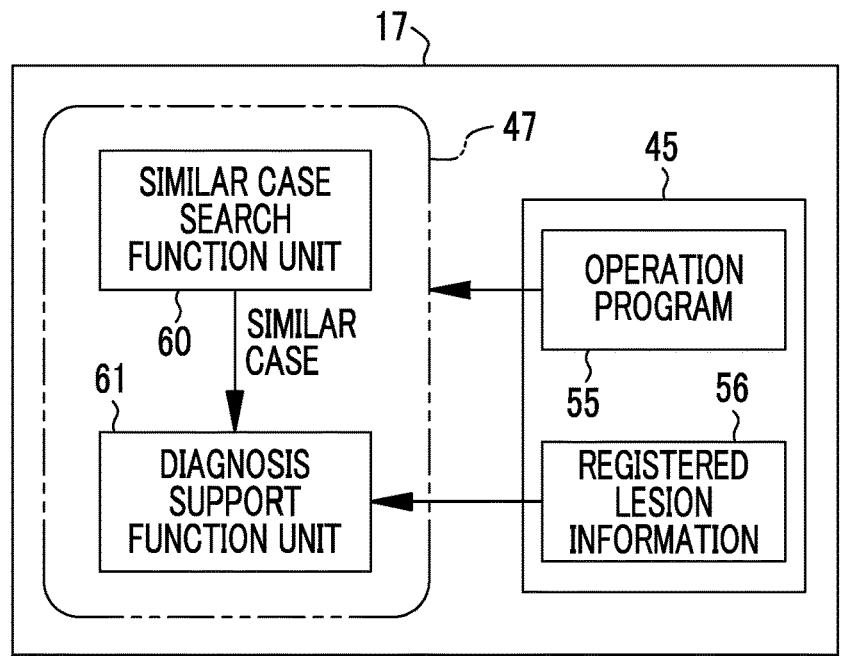
FIG. 8 is a block diagram illustrating functions of a CPU of the diagnosis support server.
FIG. 9 is a diagram illustrating the content of registered lesion information.

The types of lesions include not only the frosted glassy shadow the infiltrative shadow, but also a tumor shadow, a nodule shadow, a reticular shadow, a linear shadow, a dot shadow, a honeycomb lung, a cyst, emphysema, pneumothorax, a bulla, a cavity, bronchial wall thickening, bronchodilatation, traction bronchodilation, airbronchgram, pleural thickening, and pleural effusion (refer to FIG. 9).

A feature amount Z includes a plurality of types as indicated by ZC11, ZC21, ZC31, . . . in FIG. 2. A multi-dimensional vector having the plurality of types of feature amounts Z is referred to as a feature vector. The feature amounts ZC include, for example, a feature amount regarding a size of a lesion such as an area of the lesion, a proportion of the lesion occupying the entirety, or a long diameter and a short diameter of the lesion, a feature amount regarding a position of a lesion such as a distance from another lesion, a distance from a chest wall, or a lung lobe to which the lesion belongs such as an upper lobe, a middle lobe, a lower lobe, S1, and S2, and a feature amount regarding a density such as an average value or a standard deviation of a density (pixel value) of a lesion. The above feature amounts are example of feature amounts common to respective lesions regardless of the types of lesions. Depending on the type of lesion, there is a case where feature amounts such as an unevenness degree of a lesion periphery, a density gradient of an interface between a lesion and a normal portion, the extent of spicula such as the number or a size thereof, and a size of a cavity may be individually added thereto. A number of the uppermost digit among numbers added to the feature amount ZC in FIG. 2 indicates the type of feature amount, and a number after the uppermost digit is the same as a number of a lesion ID, and indicates a lesion having the lesion ID and the feature amount ZC. This is also the same for a feature amount ZT (refer to FIG. 10) of a target lesion.

The image reading report information is information regarding an image reading report created by the doctor DR in the past image reading. The image reading report information includes a report ID for identifying each image reading report, findings, and a disease name. The findings and the disease name are results of the doctor DR reading the case image 20C. The findings describe a position, a size, and type of lesion present in the case image 20C in text. The disease name is an illness name diagnosed by the doctor DR on the basis of the findings. FIG. 2 illustrates an example in which "a frosted glassy shadow in the left middle lobe . . . " is registered as the findings, and bacterial pneumonia is registered as the disease name.

Figure 3:
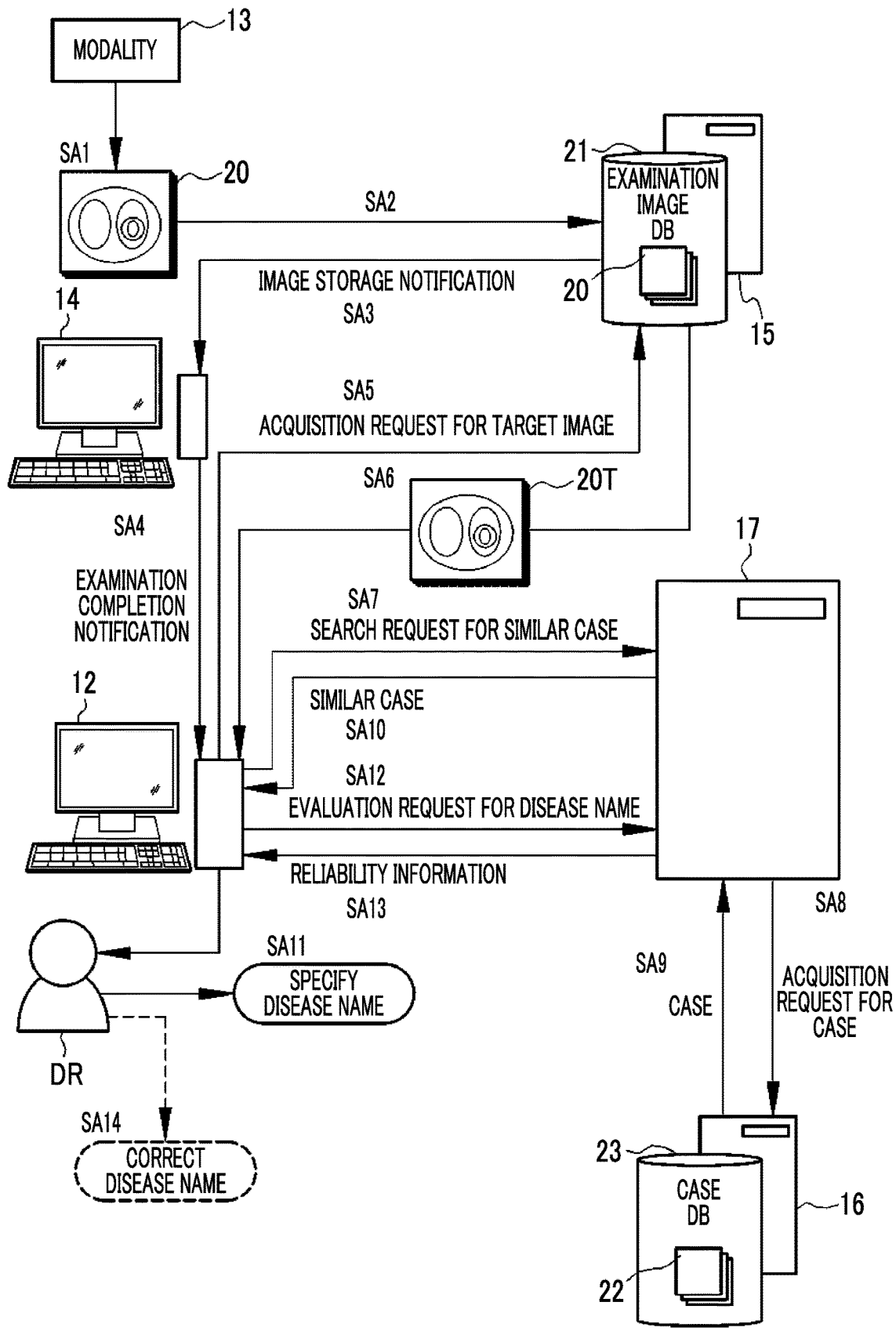
FIG. 3 is a diagram for explaining a flow until a disease name is specified from an examination.

FIG. 3 illustrates a flow until a disease name is specified from an examination. First, the modality 13 performs imaging according to an examination order, and thus the examination image 20 is output from the modality 13 (step SA1). The examination image 20 is transmitted from the modality 13 to the examination image DB server 15, and is stored in the examination image DB 21 by the examination image DB server 15 (step SA2).

The examination image DB server 15 transmits an image storage notification indicating that the examination image 20 is stored in the examination image DB 21, to the order management terminal 14 (step SA3). If the image storage notification is received, the order management terminal 14 transmits an examination completion notification to the medical care department terminal 12 having issued the examination order (step SA4). The image storage notification and the examination completion notification are added with an image ID of the examination image 20 or an order ID.

The doctor DR checks the examination completion notification through the medical care department terminal 12, and starts to read the examination image 20 including the image ID or the order ID added to the examination completion notification. Hereinafter, the examination image 20 which is an image reading target will be referred to as a target image 20T.

The doctor DR transmits an acquisition request for the target image 20T to the examination image DB server 15 via the medical care department terminal 12 (step SA5). The examination image DB server 15 receives the acquisition request for the target image 20T, and searches for the target image 20T corresponding thereto from the examination images 20 of the examination image DB 21. The retrieved target image 20T is transmitted to the medical care department terminal 12 having transmitted the acquisition request (step SA6). The acquisition request for the target image 20T includes various items of accessory information of the examination image 20, for example, an order ID or an image ID. The examination image DB server 15 outputs the examination image 20 matching the order ID or the image ID of the acquisition request as the target image 20T.

The doctor DR views the target image 20T through the medical care department terminal 12. In a case where a patient is suffering from a certain disease, a lesion (hereinafter, referred to as a target lesion) showing symptoms of the disease is present in the target image 20T. In a case where the target lesion is recognized, the doctor DR transmits a search request for a similar case to the diagnosis support server 17 via the medical care department terminal 12 for reference in specifying a disease name (step SA7). The similar case is a case 22 including the case image 20C similar to the target image 20T.

The diagnosis support server 17 receives the search request for the similar case. The diagnosis support server 17 transmits the acquisition request for the case 22 to the case DB server 16 (step SA8). The case DB server 16 receives the acquisition request for the case 22, and transmits all of the cases 22 in the case DB 23 to the diagnosis support server 17 (step SA9). The diagnosis support server 17 searches for the case 22 including the case image 20C similar to the target image 20T, that is, a similar case from all of the cases 22. The diagnosis support server 17 transmits the retrieved similar case to the medical care department terminal 12 having transmitted the search request (step SA10).

The doctor DR views the similar case through the medical care department terminal 12. The doctor DR specifies a disease name on the basis of the target lesion which is found through visual recognition of the target image 20T, the similar case from the diagnosis support server 17, and medical knowledge and experiences thereof (step SA11). In a case where the disease name specified by the doctor DR is entered to the medical care department terminal 12, and a predetermined operation which will be described later is performed, an evaluation request for the specified disease name is transmitted to the diagnosis support server 17 from the medical care department terminal 12 (step SA12).

The diagnosis support server 17 receives the evaluation request for the disease name. The diagnosis support server 17 transmits reliability information regarding the reliability of the disease name to the medical care department terminal 12 having transmitted the evaluation request (step SA13).

The doctor DR views the reliability information through the medical care department terminal 12. The doctor DR uses the disease name specified in step SA11 or corrects the disease name specified in step SA11 according to the content of the reliability information (step SA14).

Figure 4:
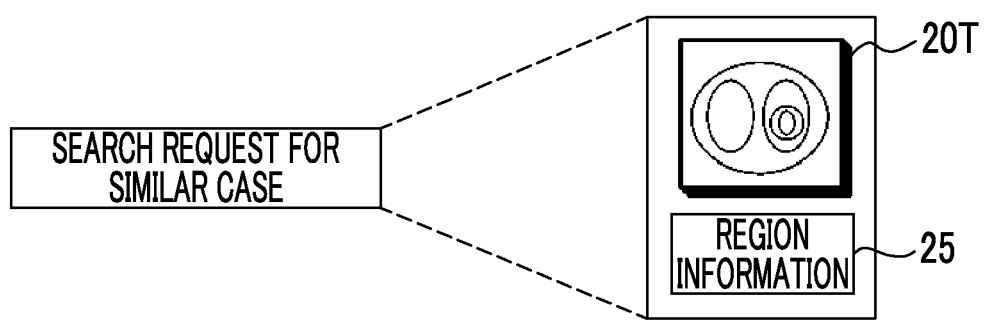
FIG. 4 is a diagram illustrating the content of a similar case search request.
Figure 5:
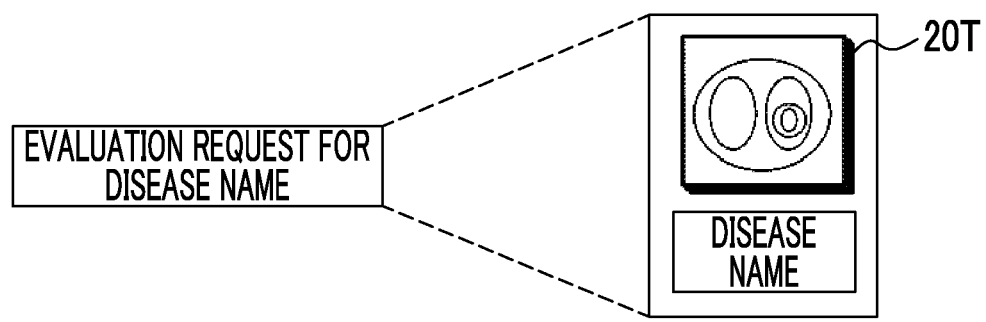
FIG. 5 is a diagram illustrating the content of a disease name evaluation request.

In FIG. 4, the search request for a similar case transmitted from the medical care department terminal 12 to the diagnosis support server 17 includes the target image 20T and region information 25. The region information 25 is information regarding a region of interest ROI (refer to FIG. 6) in the target image 20T designated by the doctor DR via the medical care department terminal 12. The region information 25 is, for example, coordinate information in which positions of pixels forming the target image 20T are expressed by two-dimensional or three-dimensional coordinates. In FIG. 5, the evaluation request for a disease name transmitted from the medical care department terminal 12 to the diagnosis support server 17 includes the target image 20T and the disease name.

Figure 6:
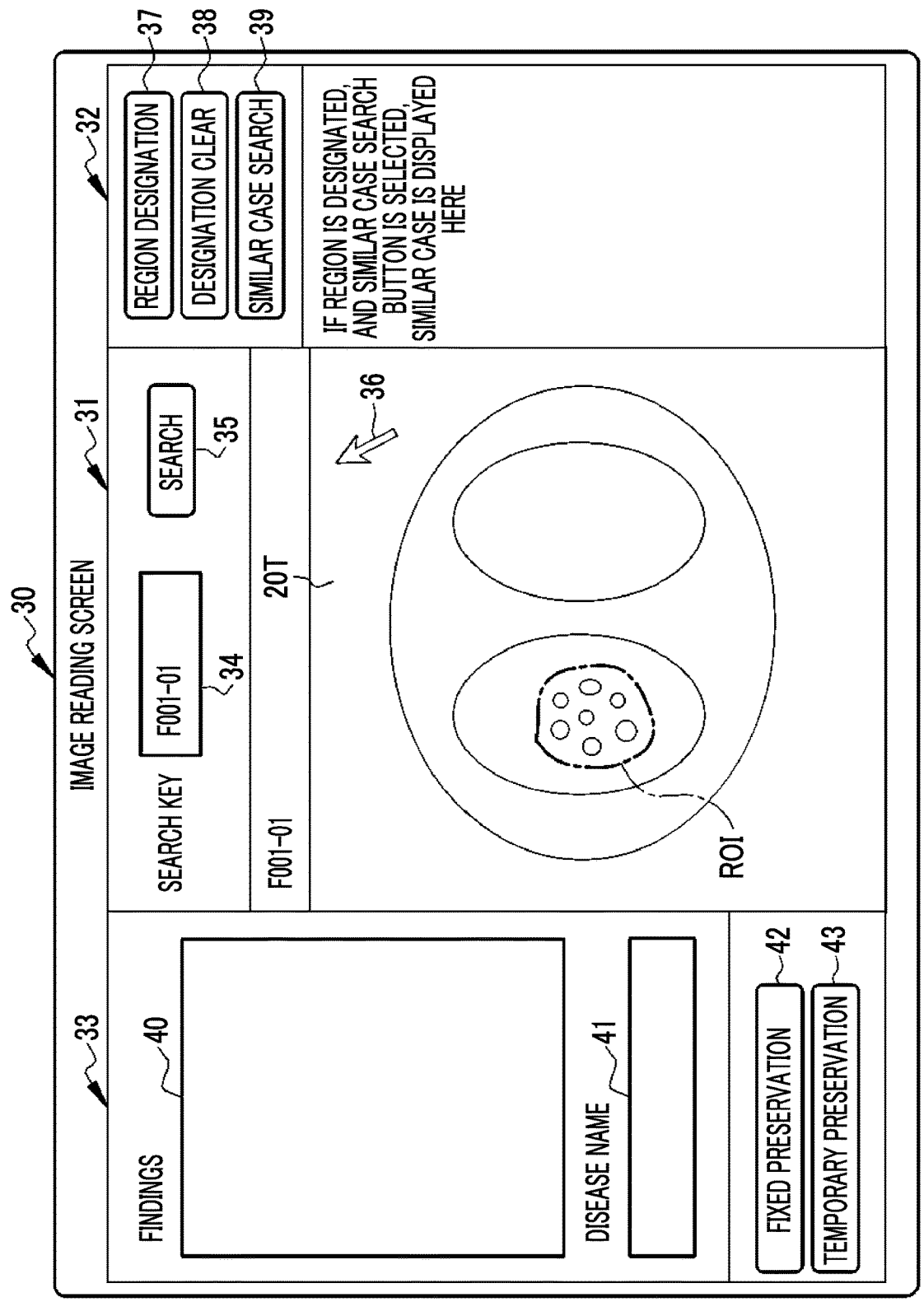
FIG. 6 is a diagram illustrating an image reading screen which is displayed in a case where a target image is read.

The target image 20T is read by using an image reading screen 30 illustrated in FIG. 6. The image reading screen 30 is used to for the doctor DR to view the target image 20T from the examination image DB server 15, and the similar case the reliability information from the diagnosis support server 17 and to create an image reading report, and is displayed on a display of the medical care department terminal 12.

The image reading screen 30 includes an image display region 31, a similar case display region 32, and a report creation region 33. The image display region 31 is disposed at the center, the similar case display region 32 is disposed on the right, and the report creation region 33 is disposed on the left. An arrangement layout or occupation areas of the regions 31 to 33 may be freely changed by the doctor DR.

The image display region 31 is provided with an entry box 34 for entering an image ID or an order ID added to an examination completion notification, and a search button 35. If a desired image ID or an order ID is entered to the entry box 34, and then the search button 35 is selected with a cursor 36, an acquisition request for the target image 20T is transmitted to the examination image DB server 15. The target image 20T corresponding to the acquisition request and an image ID thereof are displayed in the image display region 31. In a case of a set of a plurality of target images 20T, the target images 20T displayed in the image display region 31 may switch in the set through, for example, a scroll operation or a frame feed operation.

A region designation button 37, a designation clear button 38, and a similar case search button 39 are provided on an upper part in the similar case display region 32. The region designation button 37 is an operation button for designating a region of interest ROI, and the designation clear button 38 is an operation button for canceling the designated region of interest ROI. In a case where the region designation button 37 is selected with the cursor 36, it is possible to perform a region designation operation of designating any region in the target image 20T of the image display region 31.

The region designation operation is performed, for example, by designating a plurality of control points with the cursor 36 so as to surround an outer circumference of a region including a target lesion visually recognized by the doctor DR in the target image 20T. The inside of a spline which passes through the plurality of control points and draws a smooth curve indicated by a dot chain line is designated as the region of interest ROI. In a case where a plurality of target lesions are present in the target image 20T, the doctor DR designates a region including a representative lesion which is considered to be important in discrimination of a disease, as the region of interest ROI.

If the region of interest ROI is designated by using the spline, and then the similar case search button 39 is selected with the cursor 36, a search request for a similar case including the target image 20T displayed in the image display region 31 at that time, and information regarding the region of interest ROI designated with the spline, that is, the region information 25, is transmitted to the diagnosis support server 17. The region of interest ROI may be designated in a plurality for a single target image 20T.

Figure 17:
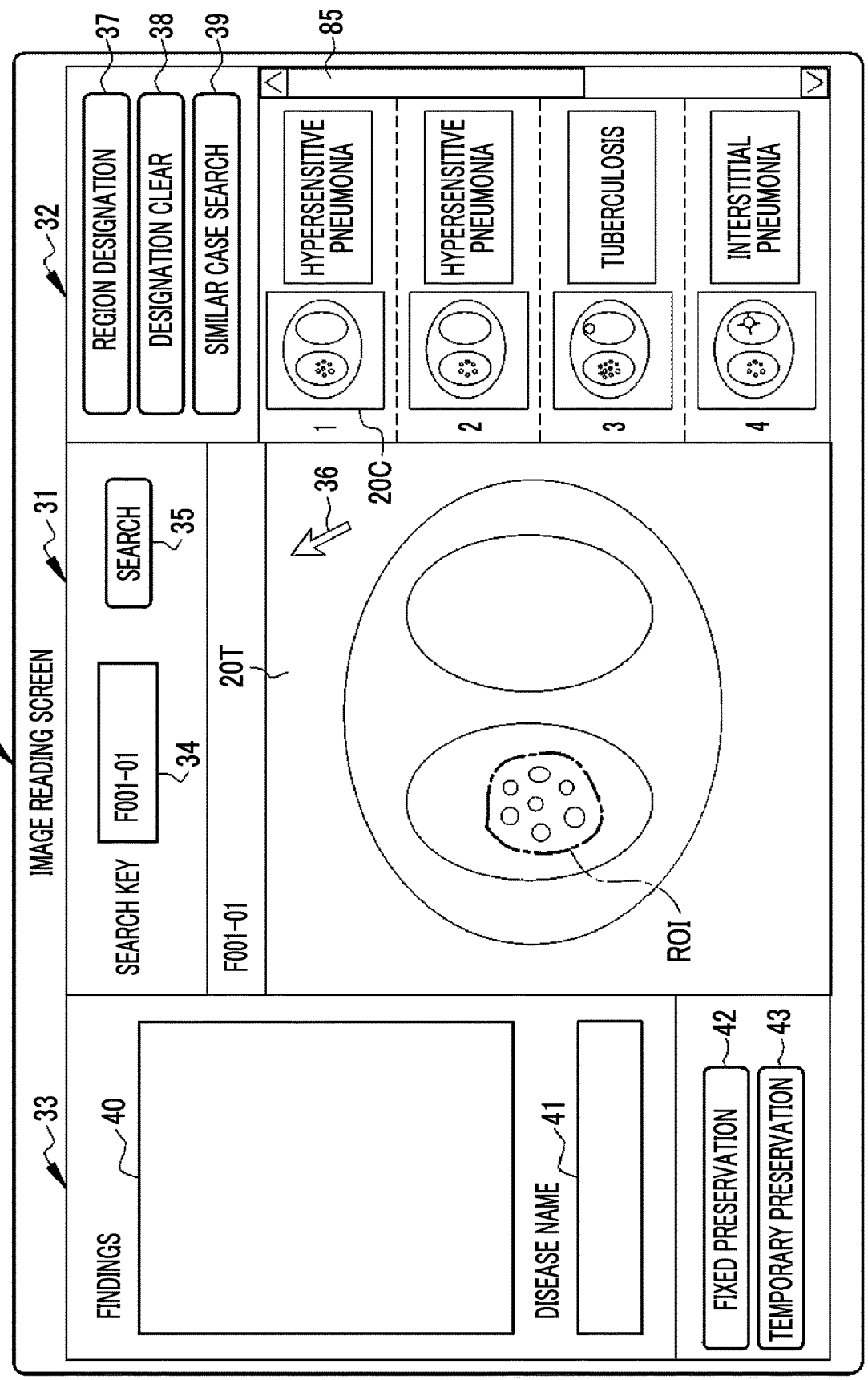
FIG. 17 is a diagram illustrating an image reading screen on which a similar case is displayed.

A similar case retrieved by the diagnosis support server 17 in response to the search request is displayed on a lower part in the similar case display region 32 (refer to FIG. 17).

The report creation region 33 is provided with a findings entry box 40 and a disease name entry box 41. A fixed preservation button 42 and a temporary preservation button 43 are provided on a lower part in the report creation region 33. If the fixed preservation button 42 is selected with the cursor 36, an evaluation request for a disease name including the target image 20T displayed in the image display region 31 and the disease name entered to the entry box 41 at that time is transmitted to the diagnosis support server 17. If the temporary preservation button 43 is selected, findings entered to the entry box 40 and a disease name entered to the entry box 41 at that time are temporarily preserved in, for example, a storage device of the medical care department terminal 12.

Figure 7:
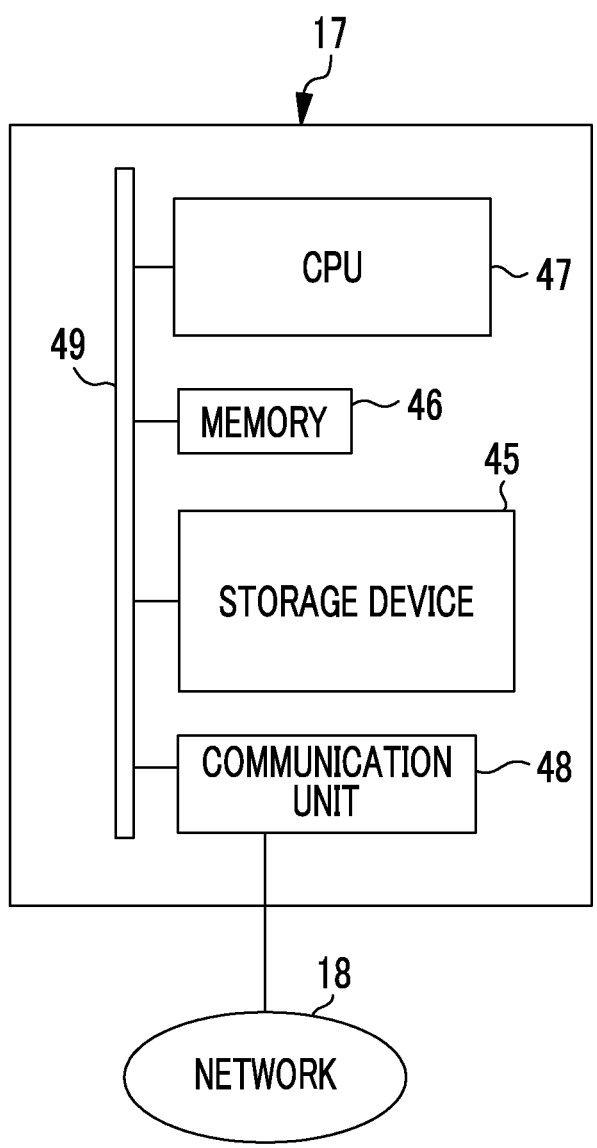
FIG. 7 is a block diagram illustrating a computer forming a diagnosis support server.

In FIG. 7, a computer forming the diagnosis support server 17 includes a storage device 45, a memory 46, a central processing unit (CPU) 47, and a communication unit 48. These constituent elements are connected to each other via a data bus 49.

The storage device 45 is a hard disk drive built into the computer forming the diagnosis support server 17, or connected via a cable or a network, or a disk array in which a plurality of hard disk drives are continuously provided. The storage device 45 stores a control program such as an operating system, various application programs (hereinafter, abbreviated to as APs), and various pieces of data accompanying the programs.

The memory 46 is a work memory for the CPU 47 executing a process. The CPU 47 loads the programs stored in the storage device 45 to the memory 46, and generally controls each unit of the computer by executing processes according to the programs.

The communication unit 48 is a network interface which performs transmission control of various pieces of information with the medical care department terminal 12 or the like via a network 18. The communication unit 48 receives the case 22 from the case DB server 16, receives a search request for a similar case and an evaluation request for a disease name from the medical care department terminal 12, and transmits an acquisition request for the case 22 to the case DB server 16, and transmits a similar case and reliability information to the medical care department terminal 12.

In FIG. 8, an operation program 55 is stored in the storage device 45 of the diagnosis support server 17 as an AP. The operation program 55 is an AP for causing the computer forming the diagnosis support server 17 to function as a similar case search apparatus and a diagnosis support apparatus. In addition to the operation program 55, registered lesion information 56 (refer to FIG. 9) is stored in the storage device 45.

If the operation program 55 is activated, the CPU 47 of the diagnosis support server 17 builds a similar case search function unit 60 functioning as a similar case search apparatus and a diagnosis support function unit 61 functioning as a diagnosis support apparatus in cooperation with the memory 46 or the like.

In FIG. 9, a disease name and a registered lesion which is a lesion corresponding to the disease name are registered in the registered lesion information 56. For example, a frosted glassy shadow and an infiltrative shadow are registered in bacterial pneumonia. The registered lesion information 56 is created by examining a correspondence relationship between the type of lesion and a disease in advance by referring to all the cases 22 stored in the case DB 23, and by gathering opinions or the latest medical knowledge of the doctor DR. Regarding a registered lesion, a lesion such as a honeycomb lung of interstitial pneumonia is registered in only a specific disease name, and a lesion such as an infiltrative shadow is registered in a plurality of disease names in common.

Figure 10:
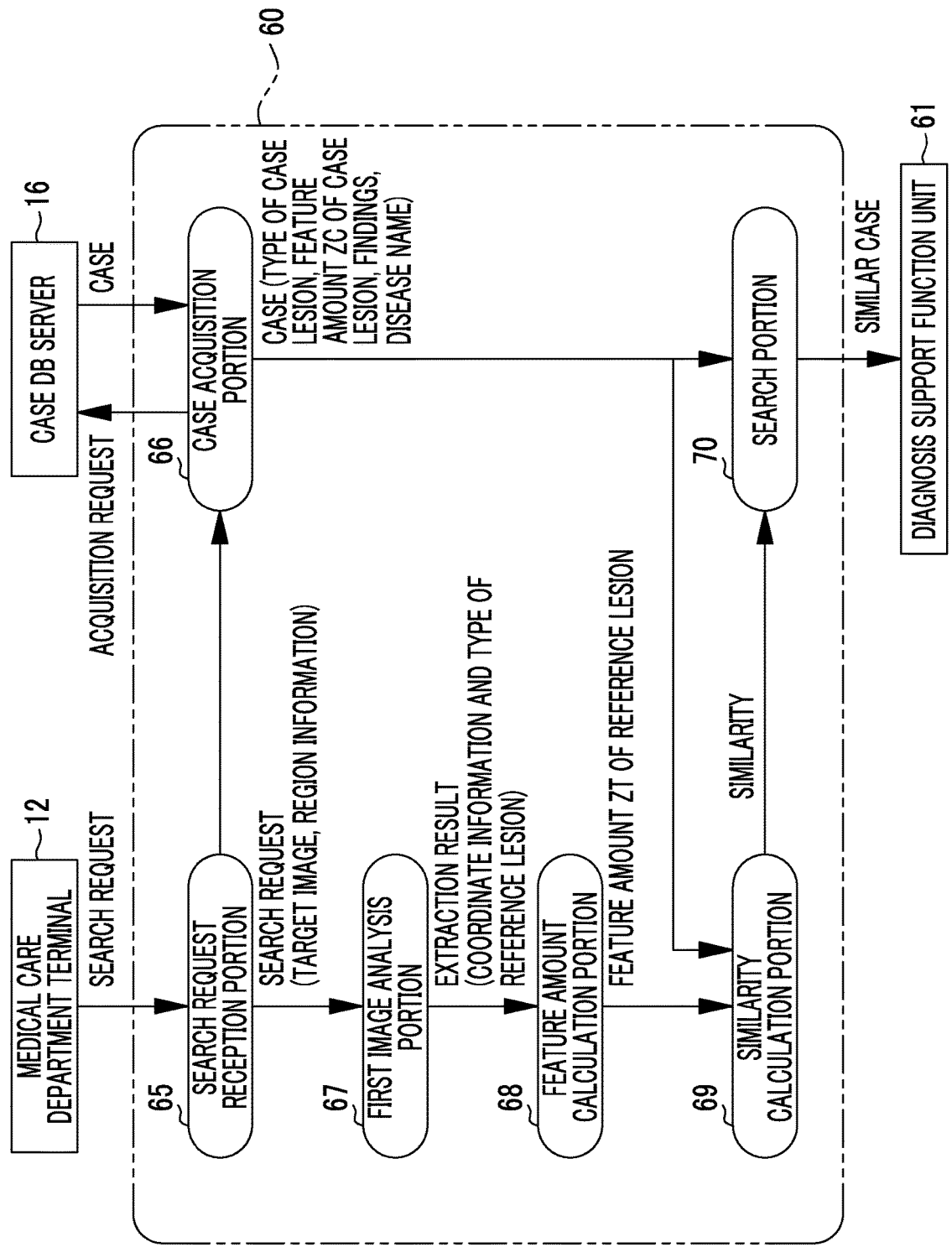
FIG. 10 is a block diagram of a similar case search function unit.

As illustrated in FIG. 10, the similar case search function unit 60 includes a search request reception portion 65, a case acquisition portion 66, a first image analysis portion 67, a feature amount calculation portion 68, a similarity calculation portion 69, and a search portion 70.

The search request reception portion 65 receives a search request for a similar case from the medical care department terminal 12. The search request reception portion 65 outputs a notification indicating that the search request for a similar case has been received, to the case acquisition portion 66. The search request reception portion 65 outputs the search request for a similar case to the first image analysis portion 67.

In a case where the notification indicating that the search request for a similar case has been received is received from the search request reception portion 65, the case acquisition portion 66 outputs an acquisition request for the case 22 to the case DB server 16. The case 22 transmitted from the case DB server 16 in response to the acquisition request is acquired. The case acquisition portion 66 outputs the case 22 to the similarity calculation portion 69 and the search portion 70.

The first image analysis portion 67 performs image analysis on the region of interest ROI indicated by the region information 25 included in the search request for a similar case so as to extract a target lesion in the region of interest ROI. The first image analysis portion 67 specifies the type of target lesion in the region of interest ROI in the process of extracting the target lesion in the region of interest ROI. Hereinafter, the target lesion in the region of interest ROI extracted by the first image analysis portion 67 will be referred to as a reference lesion.

First, the first image analysis portion 67 divides the region of interest ROI into a plurality of small regions, for example, square regions corresponding to several pixels. Next, a feature amount regarding a density of each separate small region, for example, an average value, the maximum value, the minimum value, the most frequent value, or a standard deviation of densities is calculated.

Next, the type of lesion in which each small region is included is specified on the basis of the calculated feature amounts. It is specified that each small region corresponds to any of a normal lung field, the artery, a chest wall, and the mediastinum. For example, a machine learning algorithm such as Adaptive Boosting (AdaBoost) or Deep Learning is used for this specifying. In other words, sets of lesions whose types are fixed and feature amounts thereof, sets of a normal lung field, the artery, a chest wall, and the mediastinum and feature amounts thereof, or the examination images 20 are input in a plurality as sample data so that a relationship between the type and a feature amount is learned, and thus the type corresponding to a calculated feature amount is returned. The image analysis may be performed stepwise, for example, a chest wall, the mediastinum, and the like is first identified from a lung, a normal lung field is identified from a lesion portion, and the type of lesion portion is specified.

Finally, a group of small regions specified as the same type is extracted as a single reference lesion (the same applies to a normal lung field, the artery, a chest wall, the mediastinum, and the like). The first image analysis portion 67 adds a lesion ID to the extracted reference lesion, and outputs a result of coordinate information of the reference lesion and the specified type being correlated with the lesion ID to the feature amount calculation portion 68 as an extraction result. Coordinate information of the normal lung field, the artery, the chest wall, the mediastinum, and the like is also output to the feature amount calculation portion 68 as extraction results.

The feature amount calculation portion 68 calculates a feature amount ZT of the reference lesion. In a case where there are a plurality of reference lesions, the feature amount calculation portion 68 calculates the feature amount ZT of each of the plurality of reference lesions. The feature amount calculation portion 68 outputs the calculated feature amount ZT of the reference lesion to the similarity calculation portion 69.

The similarity calculation portion 69 calculates the similarity between the case image 20C and the target image 20T on the basis of the feature amount ZC of the case lesion from the case acquisition portion 66 and the feature amount ZT of the reference lesion from the feature amount calculation portion 68. The similarity calculation portion 69 calculates the similarity of each set of the case images 20C and the target images 20T of all of the cases 22. The similarity calculation portion 69 outputs the calculated similarity to the search portion 70.

The similarity calculation portion 69 calculates a similarity according to, for example, a method disclosed in JP2015-191285A (corresponding to US2017011199A1). In the method disclosed in JP2015-191285A, first, an individual similarity between a case lesion and a reference lesion is calculated, and a comprehensive similarity between the case image 20C and the target image 20T is calculated on the basis of the calculated individual similarity. In a case where there are a plurality of case lesions and a plurality of reference lesions, the individual similarity is calculated for each set of the case lesions and the reference lesions. For example, in a case where there are three case lesions and three reference lesions, individual similarities of 3×3=9 are calculated.

For example, a square root of a sum total of the square of differences (ZTi-ZCi) between a plurality of types of feature amounts ZTi (where i is the type of feature amount) of a reference lesion and a plurality of types of feature amounts ZCi of a case lesion, that is, a distance between a feature vector having the feature amounts ZTi as elements and a feature vector having the feature amounts ZCi as elements is calculated as the individual similarity. In this case, it can be said that, as a value of the individual similarity is smaller (a distance between the feature vector having the feature amounts ZTi as elements and the feature vector having the feature amounts ZCi is shorter), the similarity between a reference lesion and a case lesion becomes higher. For example, a sum total of individual similarities is calculated as the comprehensive similarity. Values of the feature amounts ZTi and ZCi are adjusted as necessary, for example, by normalizing the feature amounts before the individual similarity is calculated, and by multiplying the square of the difference (ZTi-ZCi) by an appropriate coefficient Wi.

Only the individual similarity between a reference lesion and a case lesion of the same type may be calculated. In this case, an extraction result of a reference lesion in the first image analysis portion 67 is also output to the similarity calculation portion 69, and the type of case lesion from the case acquisition portion 66 is compared with the type of reference lesion included in the extraction result from the first image analysis portion 67. A correlation coefficient of the feature amount ZTi of a target lesion and the feature amount ZCi of a case lesion may be calculated as the individual similarity. In this case, on the contrary to the case of a distance between the feature vectors, as a value of the individual similarity becomes greater (there is a correlation between the feature amount ZTi and the feature amount ZCi), the similarity between a reference lesion and a case lesion becomes higher.

In order to calculate a similarity, a combination with a method disclosed in JP2016-045662A (corresponding to US2016055394A1) may be used. In the method disclosed in JP2016-045662A, a first presence probability that a certain specific type of lesion is present in the target image 20T is calculated according to a statistical method. At least one of a concurrence probability that the certain specific type of lesion is present in both of the target image 20T can the case image 20C and a non-concurrence probability that the certain specific type of lesion is present only in one of the target image 20T and the case image 20C is calculated as a similarity on the basis of the first presence probability and a second presence probability which is calculated in the same manner as the first presence probability and that the certain specific type of lesion is present in the case image 20C. The accuracy of a similarity can be further increased through a combination with this method.

The search portion 70 searches for a similar case from among all of the cases 22 transmitted from the case acquisition portion 66 on the basis of the similarity. For example, the cases 22 whose similarity is top ten are searched for as similar cases. The search portion 70 outputs the similar cases to the diagnosis support function unit 61.

Figure 11:
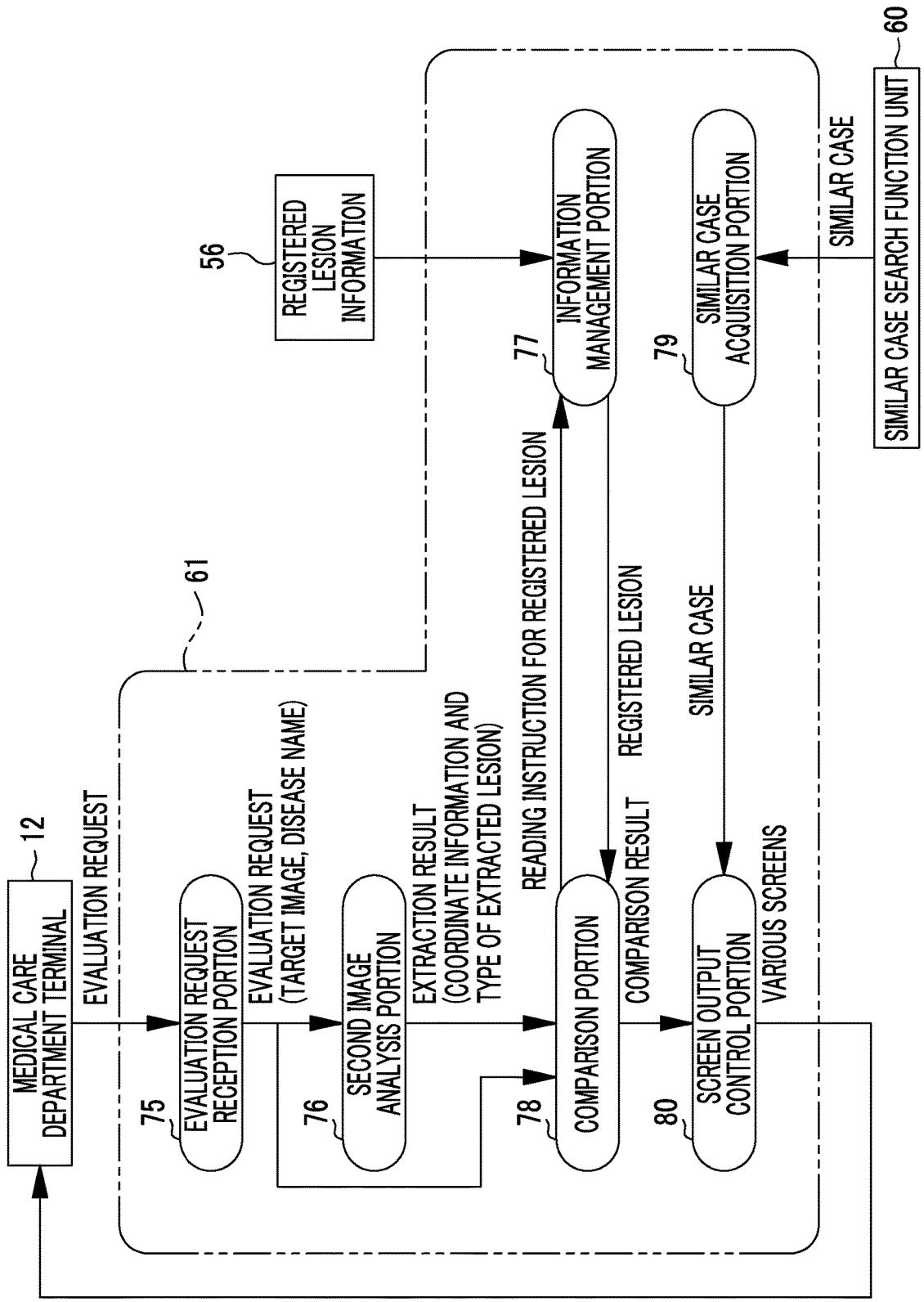
FIG. 11 is a block diagram of a diagnosis support function unit.

As illustrated in FIG. 11, the diagnosis support function unit 61 includes an evaluation request reception portion 75, a second image analysis portion 76, an information management portion 77, a comparison portion 78, a similar case acquisition portion 79, and a screen output control portion 80.

The evaluation request reception portion 75 receives an evaluation request for a disease name from the medical care department terminal 12. As illustrated in FIG. 5, the evaluation request for a disease name includes the disease name. In other words, the evaluation request reception portion 75 corresponds to a reception unit which receives entry of a disease name specified by the doctor DR visually recognizing the target image 20T, and has a reception function. The evaluation request reception portion 75 outputs the evaluation request for the disease name to the second image analysis portion 76 and the comparison portion 78.

The second image analysis portion 76 has the same configuration as that of the first image analysis portion 67 of the similar case search function unit 60, extracts a target lesion according to the same method as in the first image analysis portion 67, and specifies the type of target lesion in the process thereof.

Figure 12:
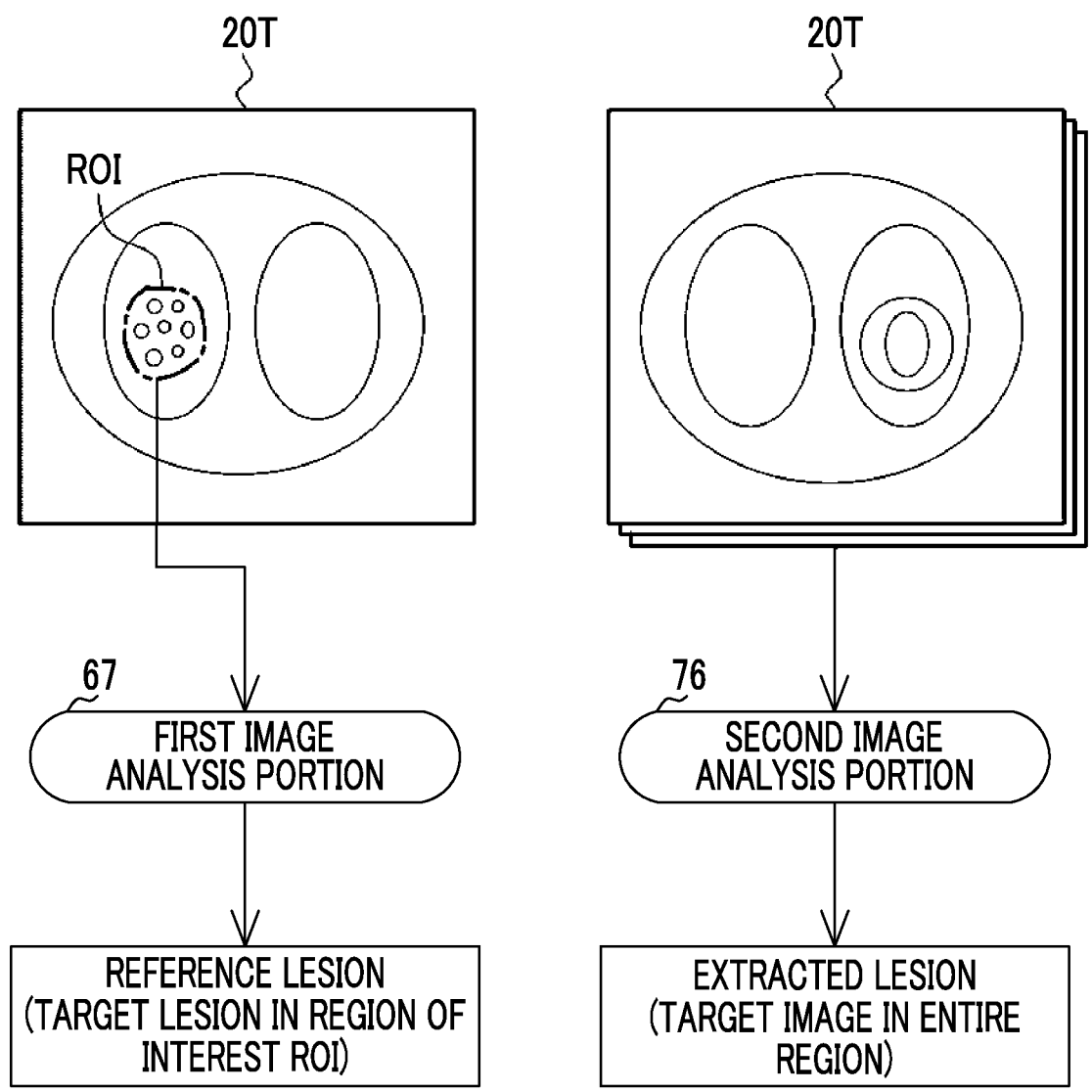
FIG. 12 is a diagram for explaining an image analysis target in each image analysis portion, and an extracted lesion.

However, image analysis targets are different from each other in the first image analysis portion 67 and the second image analysis portion 76. In other words, as illustrated on the left part in FIG. 12, the first image analysis portion 67 uses the region of interest ROI which is a partial region of the target image 20T as an image analysis target, and, as illustrated on the right part in FIG. 12, the second image analysis portion 76 uses the entire region of the target image 20T as an image analysis target. In a case where the target image 20T is a single examination image 20 such as a simple fluoroscopic image, the entire region of the target image 20T literally indicates the entire region of the single examination image 20. On the other hand, as illustrated in FIG. 12, in a case where the target image 20T is a set of a plurality of examination images 20 of tomographic images, and the region of interest ROI is a partial region of one examination image 20 thereof, all of the examination images 20 forming the set correspond to the entire region, and are image analysis targets of the second image analysis portion 76.

As mentioned above, the second image analysis portion 76 uses the entire region of the target image 20T as an image analysis target, and may thus extract not only a reference lesion extracted by the first image analysis portion 67 using the region of interest ROI as an image analysis target but also target lesions other than the reference lesion. Hereinafter, a target lesion extracted by the second image analysis portion 76 will be referred to as an extracted lesion so as to be differentiated from a reference lesion.

The second image analysis portion 76 specifies the type of extracted lesion in the process of extraction thereof, thus corresponds to a type acquisition unit which acquires the type of extracted lesion, and has a type acquisition function.

In the same manner as the first image analysis portion 67, the second image analysis portion 76 adds a lesion ID to the extracted lesion, outputs a result of coordinate information of the extracted lesion and the specified type being correlated with the lesion ID to the comparison portion 78 as an extraction result.

The information management portion 77 has an information management function of managing the registered lesion information 56. The information management portion 77 receives a reading instruction for a registered lesion from the comparison portion 78. The information management portion 77 reads a registered lesion corresponding to the reading instruction from the registered lesion information 56, and outputs the read registered lesion to the comparison portion 78.

Figure 13:
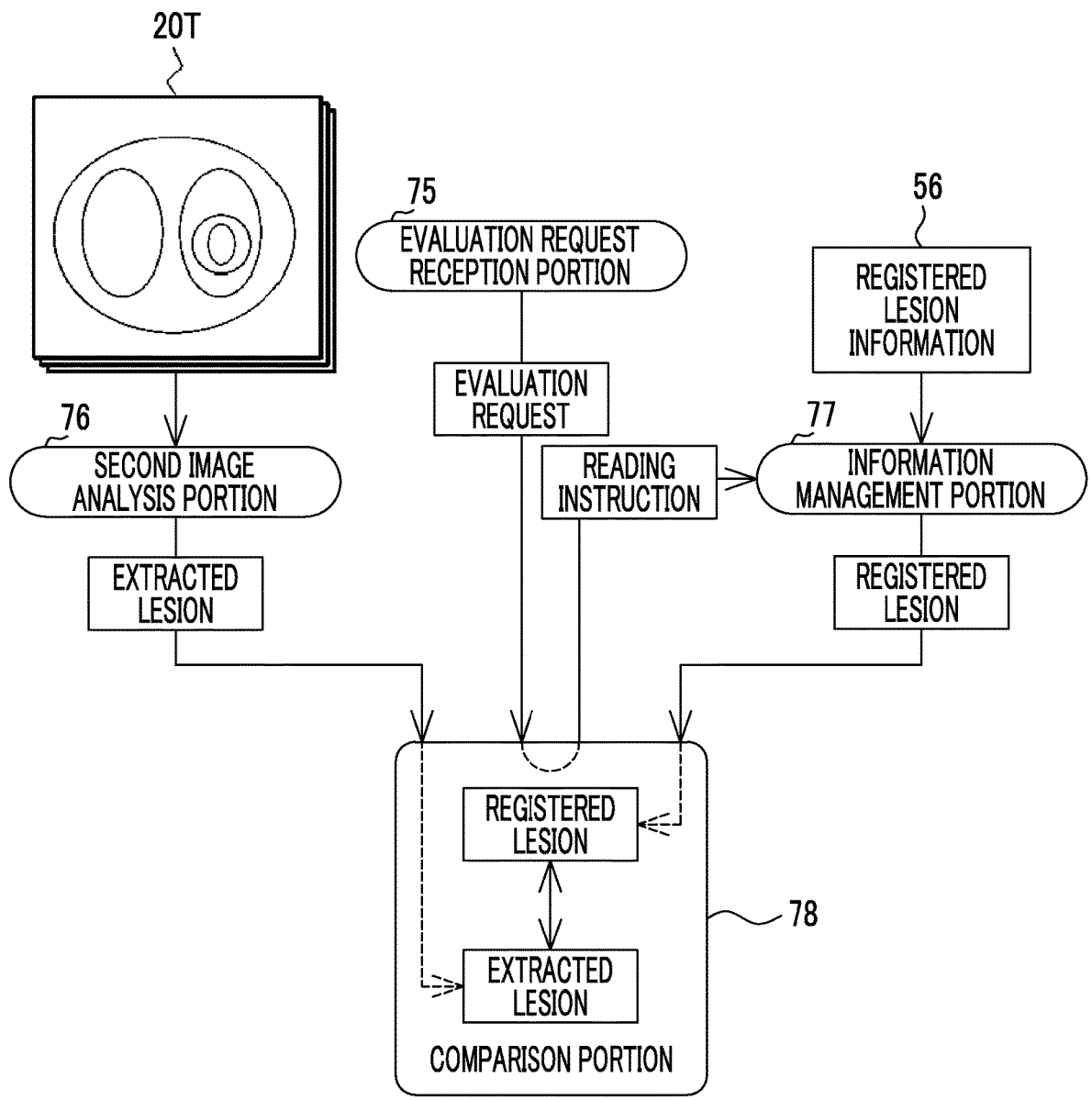
FIG. 13 is a diagram for explaining a function of a comparison unit.

The comparison portion 78 has a comparison function. Specifically, as illustrated in FIG. 13, the comparison portion 78 outputs a reading instruction for a registered lesion corresponding to the disease name included in the evaluation request from the evaluation request reception portion 75, to the information management portion 77. The registered lesion output from the information management portion 77 in response to the reading instruction is received. On the other hand, an extraction result of an extracted lesion is received from the second image analysis portion 76. The comparison portion 78 compares the type of registered lesion from the information management portion 77 with the type of extracted lesion from the second image analysis portion 76. The comparison portion 78 outputs a comparison result to the screen output control portion 80.

In a case where there are a plurality of extracted lesions of the same type, the comparison portion 78 counts a single type as the type. For example, in a case where there are three frosted glassy shadows and two reticular shadows as extracted lesions, the type of extracted lesion is two types such as the frosted glassy shadow and the reticular shadow.

Figure 14:
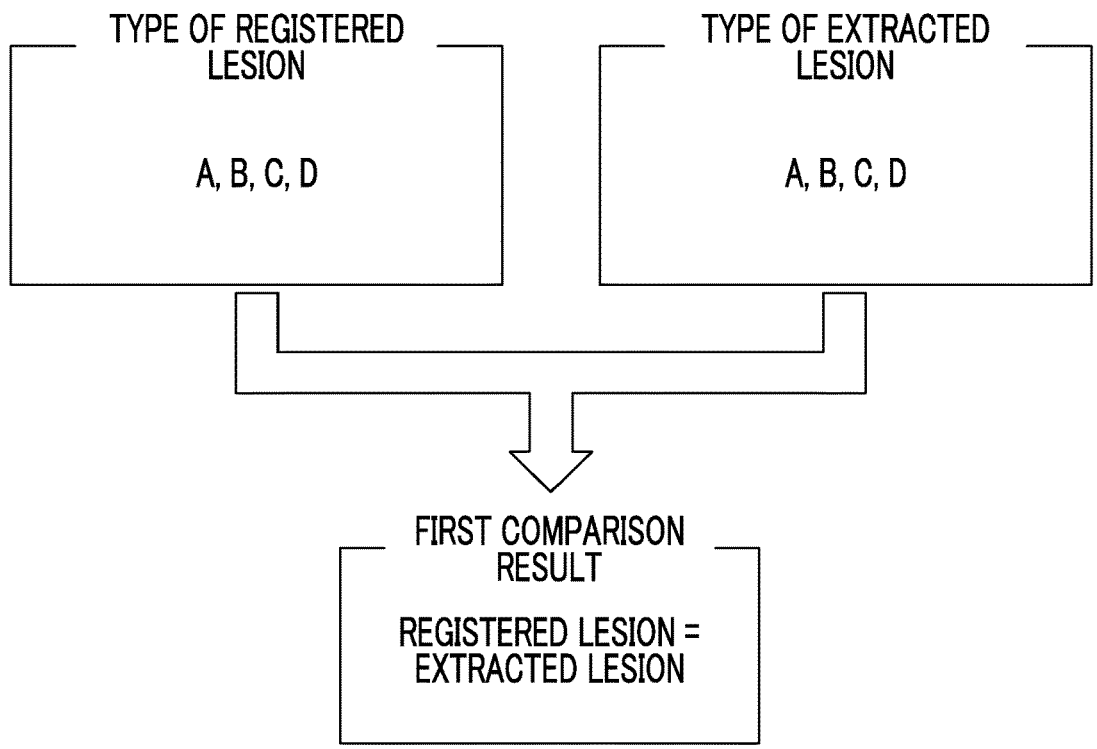
FIG. 14 is a diagram illustrating an example of a first comparison result.
Figure 15:
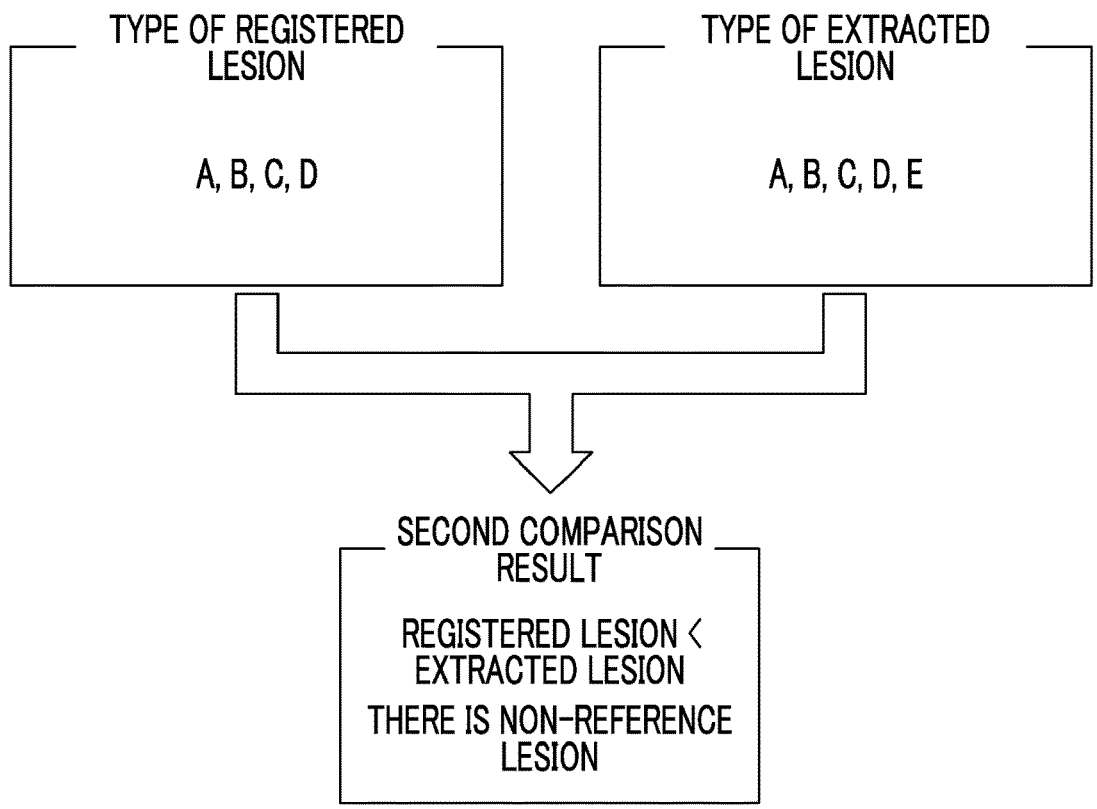
FIG. 15 is a diagram illustrating an example of a second comparison result.
Figure 16:
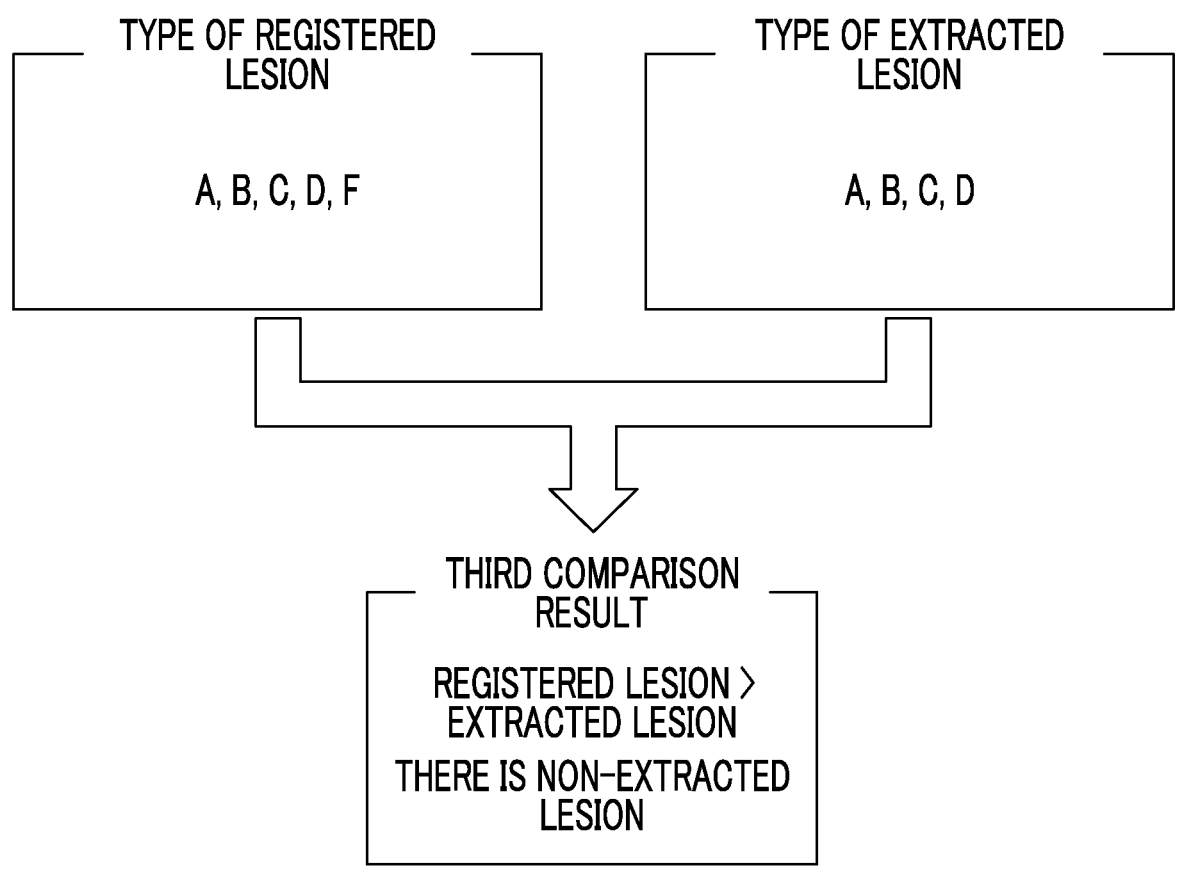
FIG. 16 is a diagram illustrating an example of a third comparison result.

The comparison portion 78 outputs three comparison results. As in a case illustrated in FIG. 14 in which both of the registered lesion and the extracted lesion have four types such as A, B, C, and D, the first comparison result is output in a case where the types of registered lesions exactly match the types of extracted lesions (registered lesions=extracted lesions). As in a case illustrated in FIG. 15 in which the types of registered lesions are A, B, C, and D, and the types of extracted lesions are A, B, C, D, and E, the second comparison result is output in a case where the extracted lesions include a non-reference lesion (in FIG. 15, the lesion E) which is not present in the registered lesions (registered lesions<extracted lesions). As in a case illustrated in FIG. 16 in which the types of registered lesions are A, B, C, D, and F, and the types of extracted lesions are A, B, C, and D, on the contrary to the second comparison result, the third comparison result is output in a case where the registered lesions include a non-extracted lesion (in FIG. 16, the lesion F) which is not present in the extracted lesions (registered lesions>extracted lesions).

The non-reference lesion is not present in the registered lesions corresponding to the disease name specified by the doctor DR, and is present in the extracted lesions which are automatically extracted by the second image analysis portion 76, and can thus be said to be a target lesion for which there is a high probability that a disease name may be specified without being taken into consideration due to overlooking of the doctor DR or a careless mistake of not perceiving the presence thereof. On the other hand, the non-extracted lesion is present in the registered lesions but is not present in the extracted lesions, and can thus be said to be a target lesion for which there is a high probability that the doctor DR may misrecognize a normal lung field as a lesion portion, and specify a disease name by taking into consideration the misrecognized lesion portion. Alternatively, the non-extracted lesion can be said to be a target lesion which cannot be extracted in terms of extraction performance of the second image analysis portion 76.

The similar case acquisition portion 79 has a similar case acquisition function of acquiring a similar case output from the search portion 70 of the similar case search function unit 60. The similar case acquisition portion 79 outputs the acquired similar case to the screen output control portion 80.

The screen output control portion 80 corresponds to an output control unit. The screen output control portion 80 displays a similar case from the similar case acquisition portion 79 in the similar case display region 32 of the image reading screen 30. In other words, as in the image reading screen 30 illustrated in FIG. 17, the screen output control portion 80 displays similar cases in order of higher similarity in a list form on the lower part in the similar case display region 32. Each of the similar cases is, specifically, a set of the case image 20C and a disease name. The case image 20C displayed in the similar case display region 32 can be selected with the cursor 36. In a case where the case image 20C is selected, for example, the case image 20C with a full size is displayed on a screen which is different from the image reading screen 30. The reference numeral 85 indicates a scroll bar for scroll-displaying similar cases which are not displayed in the similar case display region 32 together.

The screen output control portion 80 has an output control function of outputting reliability information regarding the reliability of a disease name received by the evaluation request reception portion 75 on the basis of a comparison result from the comparison portion 78.

Figure 18:
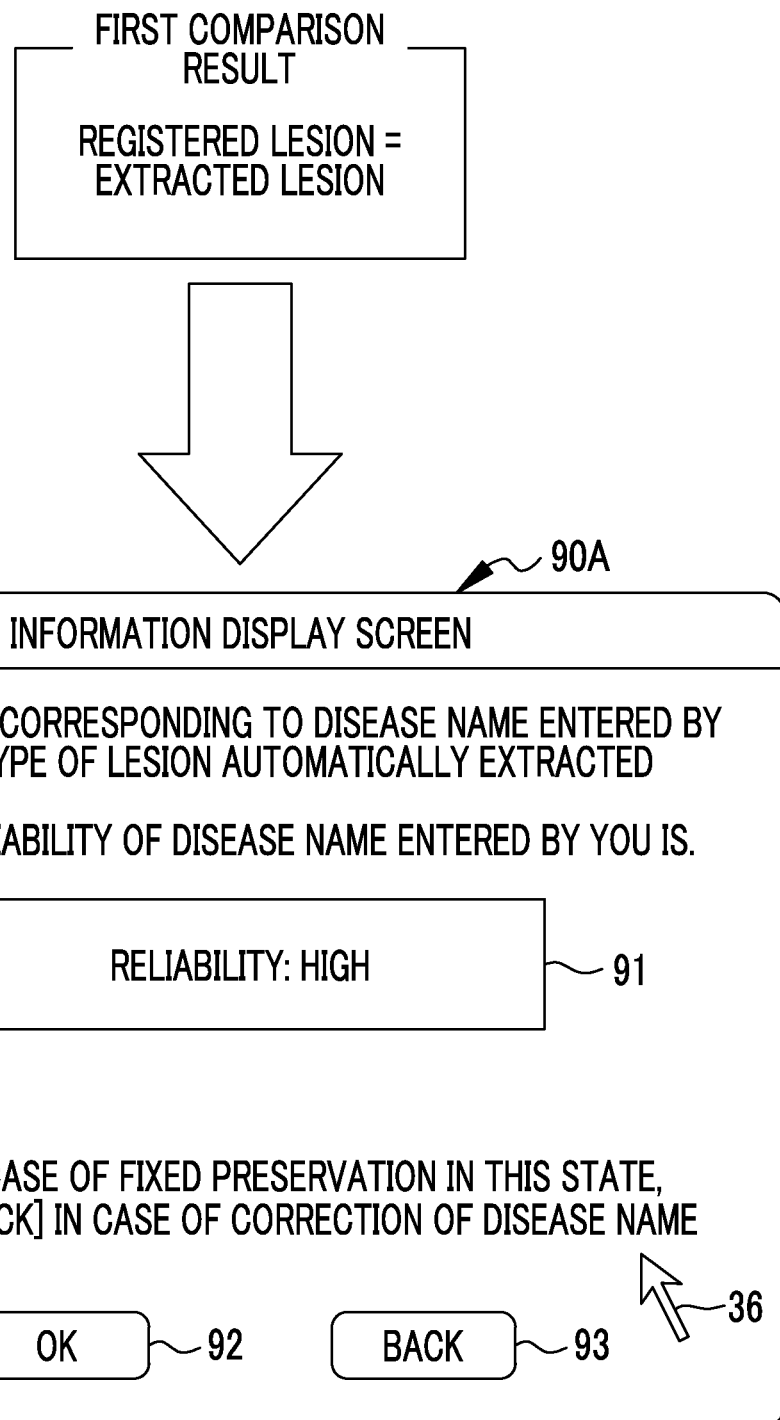
FIG. 18 is a diagram illustrating an information display screen in a case of the first comparison result.
Figure 20:
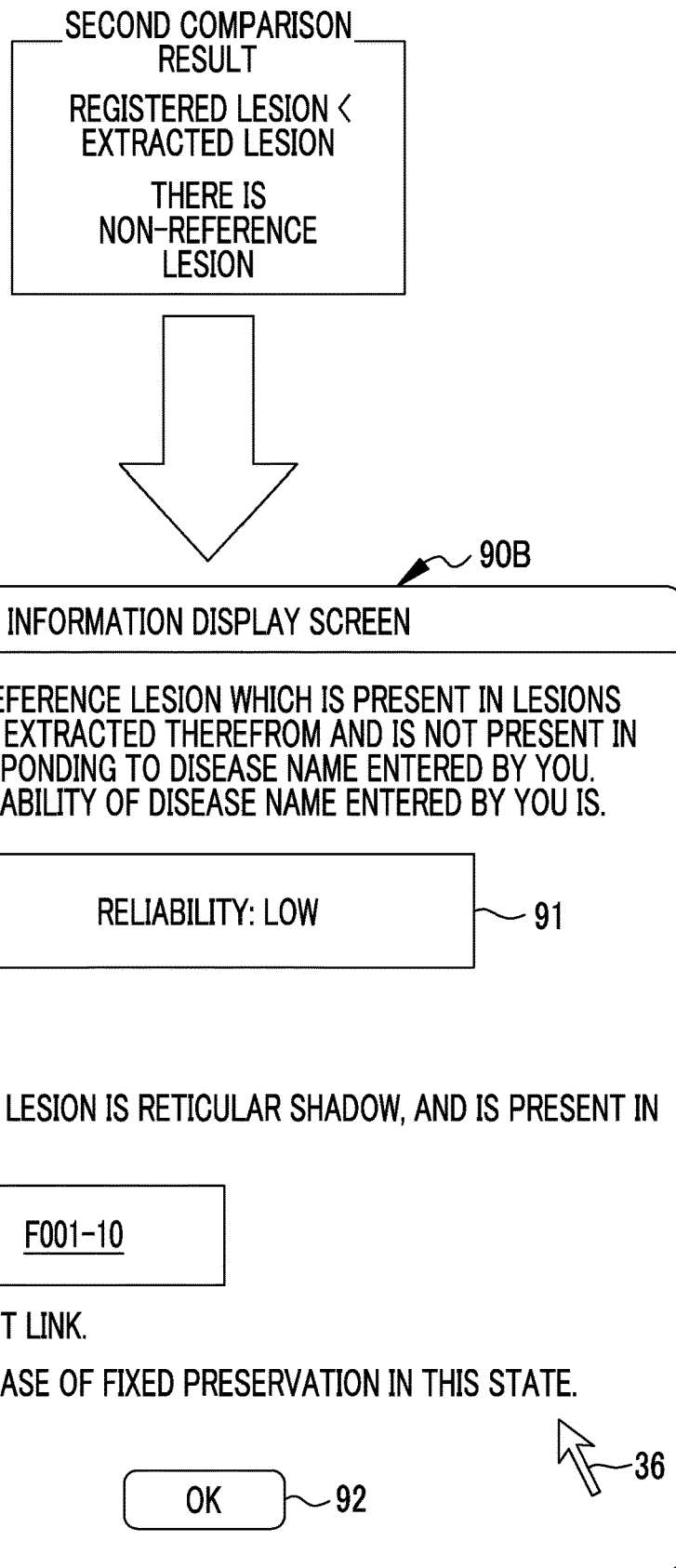
FIG. 20 is a diagram illustrating an information display screen in a case of the second comparison result.
Figure 23:
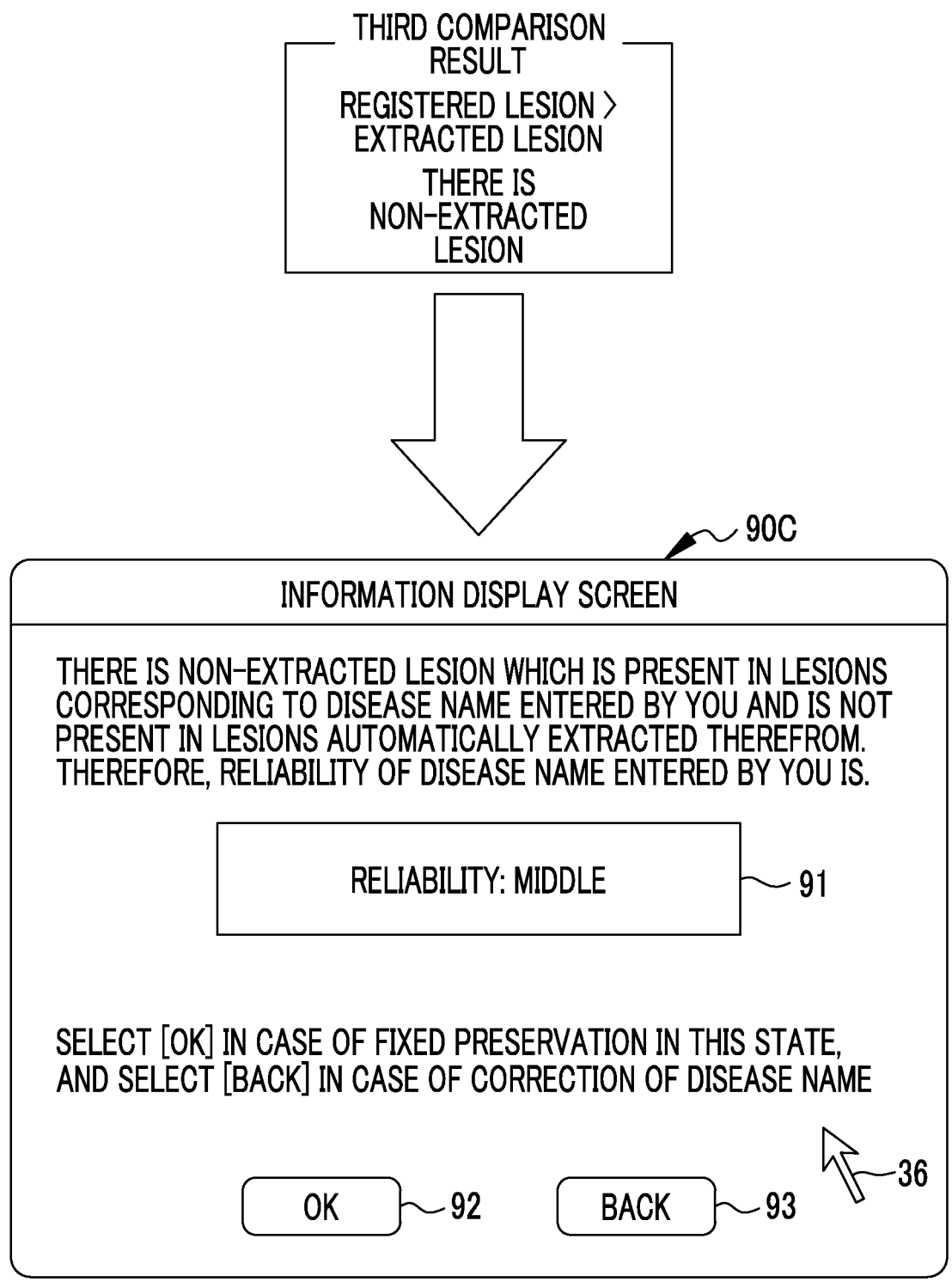
FIG. 23 is a diagram illustrating an information display screen in a case of the third comparison result.

As illustrated in FIGS. 18, 20 and 23, the screen output control portion 80 outputs information display screens 90A, 90B and 90C on which reliability information is displayed, to the medical care department terminal 12 having transmitted an evaluation request, as an aspect of output of the reliability information. The information display screens 90A to 90C are displayed in a pop-up form on the image reading screen 30 after the fixed preservation button 42 is selected in the medical care department terminal 12. Hereinafter, in a case where the screens are not particularly differentiated from each other, the information display screens 90A to 90C will be referred to as an information display screen 90.

FIG. 18 illustrates the information display screen 90A which is output in a case of the first comparison result (registered lesions=extracted lesions). The information display screen 90A displays a message indicating that the types of registered lesions match the types of extracted lesions, and a frame in which the reliability of the disease name received from the evaluation request reception portion 75 is written, that is, reliability information 91 from an upper part to an intermediate part. "Reliability: high" is recorded in the reliability information 91 in this case.

An OK button 92 and a back button 93 are provided on a lower part in the information display screen 90A. If the OK button 92 is selected with the cursor 36, the display of the information display screen 90A and the image reading screen 30 disappears, and the findings entered to the entry box 40 and the disease name entered to the entry box 41 at that time are fixedly preserved in the cases 22 as image reading report information. The fixedly preserved image reading report information is prohibited from being edited in order to prevent illicit falsification. On the other hand, if the back button 93 is selected with the cursor 36, the display of the information display screen 90A disappears, and returns to the display of the image reading screen 30 so that the findings and the disease name can be corrected.

Figure 19:
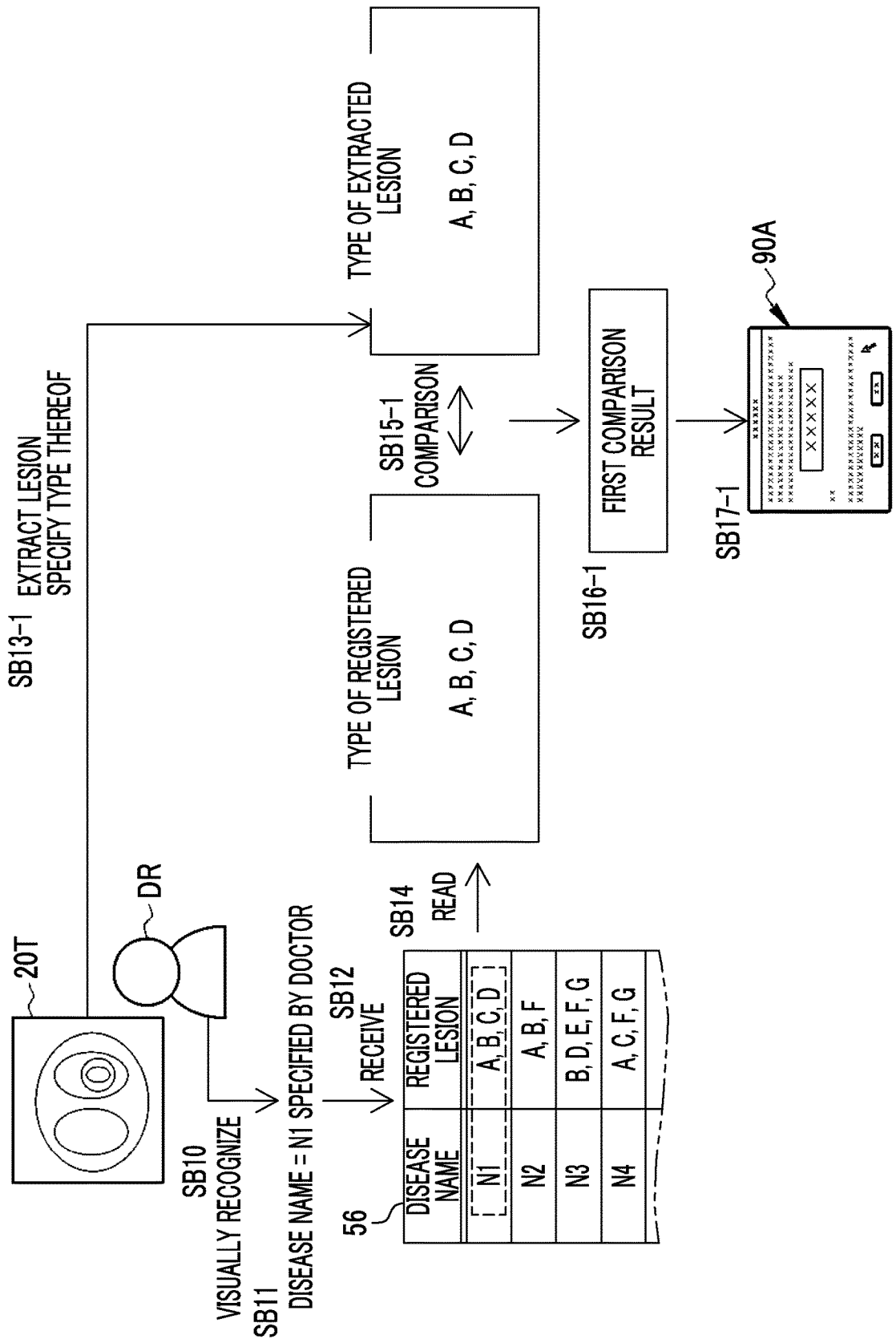
FIG. 19 is a diagram for explaining a flow until the information display screen is output in a case of the first comparison result.

FIG. 19 illustrates a schematically summarized flow until the information display screen 90A is output. First, the doctor DR visually recognizes the target image 20T on the image reading screen 30, and specifies a disease name as, for example, N1 (steps SB10 and SB11). The specified disease name N1 is entered to the entry box 41, and the fixed preservation button 42 is selected. Consequently, an evaluation request for the disease name N1 is transmitted from the medical care department terminal 12 to the diagnosis support server 17, and is received by the evaluation request reception portion 75 (step SB12).

The second image analysis portion 76 performs image analysis on the entire region of the target image 20T. Thus, extracted lesions are extracted, and the types A, B, C and D thereof are specified (step SB13-1). Extraction results of the extracted lesions are output to the comparison portion 78. On the other hand, the types A, B, C and D of registered lesions corresponding to the disease name N1 included in the evaluation request are read from the registered lesion information 56 by the information management portion 77, and are output to the comparison portion 78 (step SB14).

The comparison portion 78 compares the types A, B, C and D of registered lesions with the types A, B, C and D of extracted lesions (step SB15-1), and outputs a comparison result of the types of registered lesions exactly matching the types of extracted lesions, that is, the first comparison result to the screen output control portion 80 (step SB16-1). Consequently, the information display screen 90A is output from the screen output control portion 80 (step SB17-1).

FIG. 20 illustrates the information display screen 90B which is output in a case of the second comparison result (registered lesions<extracted lesions; there is a non-reference lesion). The information display screen 90B displays a message indicating that there is a non-reference lesion which is present in extracted lesions and is not present in registered lesions, and "reliability: low" is recorded in the reliability information 91. In other words, a warning indicating that the non-reference lesion is not referred to in specifying the disease name is displayed. The type of non-reference lesion is displayed on the information display screen 90B, and a link 94 for displaying the target image 20T in which the non-reference lesion is present is provided.

The type of non-reference lesion and the target image 20T in which the non-reference lesion is present are derived on the basis of extraction results of extracted lesions in the second image analysis portion 76 and a comparison result in the comparison portion 78. For example, in a case where extracted lesions are of five types such as A, B, C, D, and E, and registered lesions are of four types such as A, B, C, and D, it can be seen that a non-reference lesion is the lesion E on the basis of a comparison result in the comparison portion 78 (refer to FIG. 21). The target image 20T in which the lesion E is present is understood from coordinate information of an extraction result in the second image analysis portion 76. In FIG. 20, a reticular shadow is exemplified as the type of non-reference lesion, and the target image 20T having an image ID "F001-10" is exemplified as the target image 20T in which the non-reference lesion is present.

As will be described later, since the link 94 replaces the back button 93, the back button 93 is not provided on the information display screen 90B, and only the OK button 92 is provided. In a case where the doctor DR views the "reliability: low" of the reliability information 91, and is confident that a disease name specified by the doctor DR is correct, the OK button 92 is provided for fixed preservation by ignoring the display of the reliability information 91. Only the link 94 may be provided on the information display screen 90B, and the OK button 92 may not be provided.

Figure 21:
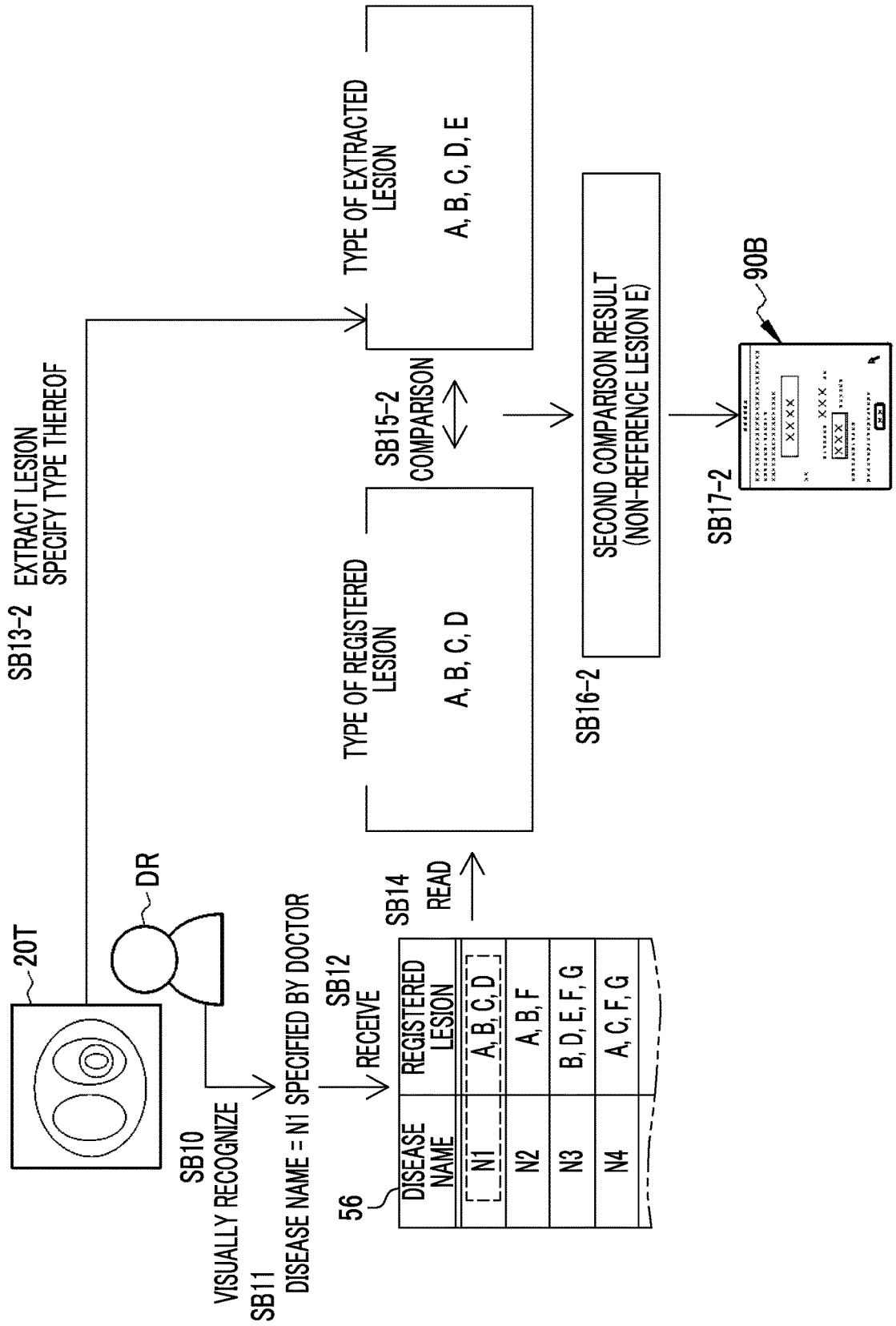
FIG. 21 is a diagram for explaining a flow until the information display screen is output in a case of the second comparison result.

FIG. 21 illustrates a schematically summarized flow until the information display screen 90B is output, in the same manner as in FIG. 19. FIG. 21 is fundamentally the same as FIG. 19, but is different therefrom in that the types of extracted lesions specified by the second image analysis portion 76 are A, B, C, D, and E (step SB13-2). The comparison portion 78 compares the types A, B, C and D of registered lesions with the types A, B, C, D and E of extracted lesions (step SB15-2), and outputs a comparison result of there being the non-reference lesion E, that is, the second comparison result to the screen output control portion 80 (step SB16-2). Consequently, the information display screen 90B is output from the screen output control portion 80 (step SB17-2).

If the link 94 on the information display screen 90B is selected with the cursor 36, the display of the information display screen 90B disappears. The display switches to the image reading screen 30 illustrated in FIG. 22.

Figure 22:
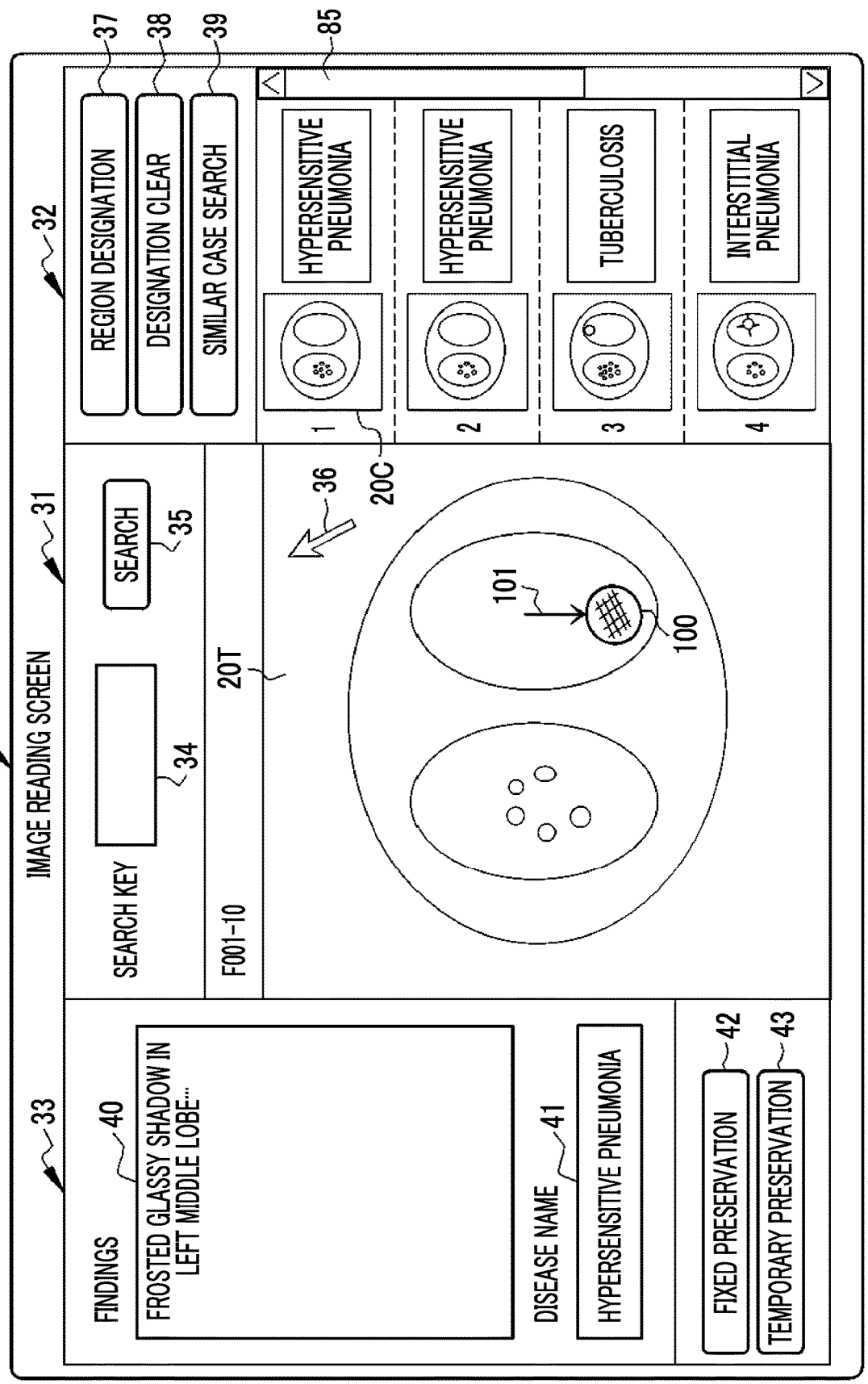
FIG. 22 is a diagram illustrating an image reading screen in a case where a link of a target image on which a non-reference lesion is present is selected.

In FIG. 22, the target image 20T (in this example, the target image 20T having an image ID "F001-10") in which the non-reference lesion is present, indicated by the link 94 on the information display screen 90B is displayed in the image display region 31 of the image reading screen 30. In other words, the image reading screen 30 illustrated in FIG. 22 corresponds to an image display screen.

In the image reading screen 30 illustrated in FIG. 22, the non-reference lesion is surrounded by a circular frame 100, and is indicated by an arrow annotation 101. In other words, the non-reference lesion and other lesions are displayed in different aspects. Regarding a method of displaying the non-reference lesion and other lesions in different aspects, the non-reference lesion and other lesions may be displayed in different colors, and the non-reference lesion may be displayed in a blinking manner.

FIG. 23 illustrates the information display screen 90C which is output in a case of the third comparison result (registered lesions>extracted lesions; there is a non-extracted lesion). The information display screen 90C displays a message indicating that there is a non-extracted lesion which is present in registered lesions and is not present in extracted lesions on the contrary to the information display screen 90B, and "reliability: middle" is recorded in the reliability information 91. The information display screen 90C is provided with the OK button 92 and the back button 93 in the same manner as the information display screen 90A.

Figure 24:
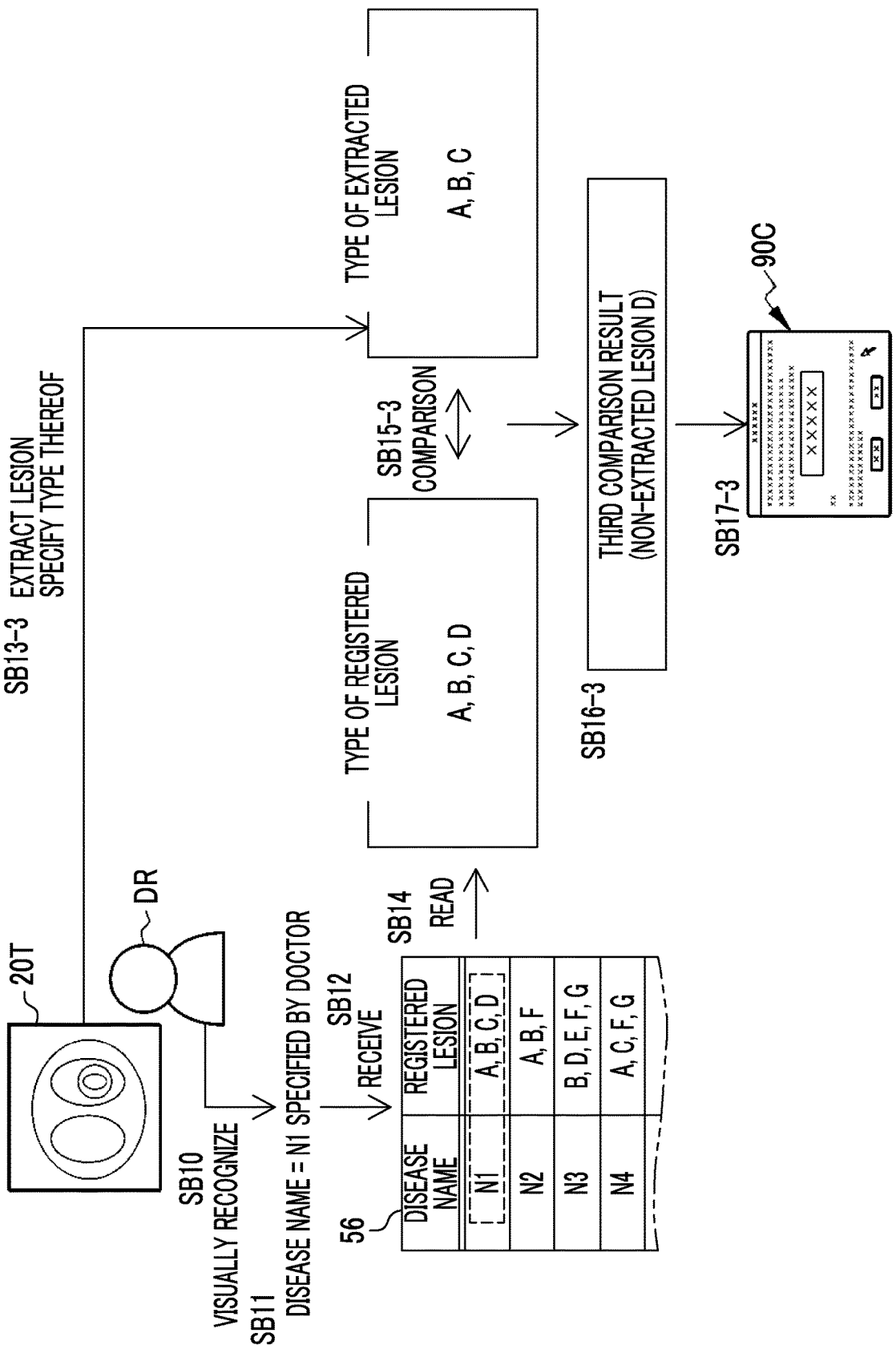
FIG. 24 is a diagram for explaining a flow until the information display screen is output in a case of the third comparison result.

FIG. 24 illustrates a schematically summarized flow until the information display screen 90C is output, in the same manner as in FIGS. 19 and 21. FIG. 24 is fundamentally the same as FIGS. 19 and 21, but is different therefrom in that the types of extracted lesions specified by the second image analysis portion 76 are A, B and C (step SB13-3). The comparison portion 78 compares the types A, B, C and D of registered lesions with the types A, B and C of extracted lesions (step SB15-3), and outputs a comparison result of there being the non-extracted lesion D, that is, the third comparison result to the screen output control portion 80 (step SB16-3). Consequently, the information display screen 90C is output from the screen output control portion 80 (step SB17-3).

The screen output control portion 80 outputs various screens such as the image reading screen 30 or the information display screen 90, for example, in a format of screen data for web distribution, created in a markup language such as Extensible Markup Language (XML). Consequently, various screens can be viewed on a web browser in the medical care department terminal 12. Other data description languages such as JavaScript (registered trademark) Object Notation (JSON) may be used instead of the XML.

Hereinafter, an operation of the diagnosis support server 17 with the above-described configuration will be described with reference to FIGS. 25 and 26. First, the operation program 55 is activated. Consequently, the similar case search function unit 60 and the diagnosis support function unit 61 are built into the CPU 47, and thus the computer forming the diagnosis support server 17 functions as a similar case search apparatus and a diagnosis support apparatus.

The doctor DR views the target image 20T on the image reading screen 30 of the medical care department terminal 12, designates the region of interest ROI as necessary, and selects the similar case search button 39. Consequently, a search request for a similar case having the case image 20C similar to the target image 20T is transmitted to the diagnosis support server 17.

Figure 25:
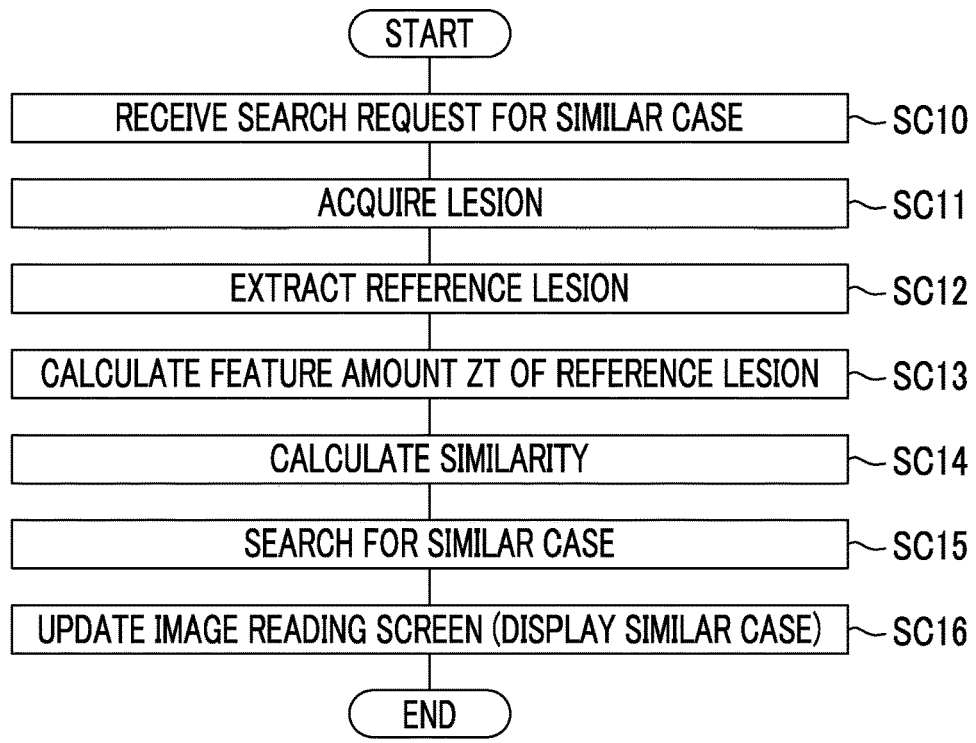
FIG. 25 is a flowchart illustrating process procedures in the similar case search function unit.

In FIG. 25 illustrating process procedures in the similar case search function unit 60, as shown in step SC10, in the diagnosis support server 17, the search request reception portion 65 receives the search request for a similar case from the medical care department terminal 12. A notification indicating that the search request for a similar case has been received is output from the search request reception portion 65 to the case acquisition portion 66, and the search request for a similar case is output from the search request reception portion 65 to the first image analysis portion 67.

An acquisition request for the case 22 is output from the case acquisition portion 66 to the case DB server 16. The case 22 transmitted from the case DB server 16 in response to the acquisition request is acquired by the case acquisition portion 66 (step SC11). The case 22 is output from the case acquisition portion 66 to the similarity calculation portion 69 and the search portion 70.

The search request for a similar case includes the region information 25 regarding the region of interest ROI. The region of interest ROI indicated by the region information 25 undergoes image analysis in the first image analysis portion 67 as illustrated on the left part in FIG. 12, and thus a target lesion in the region of interest ROI, that is, a reference lesion is extracted (step SC12). This extraction result is output from the first image analysis portion 67 to the feature amount calculation portion 68.

The feature amount calculation portion 68 calculates the feature amount ZT of the reference lesion (step SC13). The feature amount ZT of the reference lesion is output from the feature amount calculation portion 68 to the similarity calculation portion 69. Next, the similarity calculation portion 69 calculates the similarity between the case image 20C of each case 22 and the target image 20T (step SC14). The similarity is output to the search portion 70.

The search portion 70 searches for a similar case on the basis of the similarity (step SC15). The similar case is output to the similar case acquisition portion 79 of the diagnosis support function unit 61, and is also output to the screen output control portion 80 from the similar case acquisition portion 79.

As illustrated in FIG. 17, the screen output control portion 80 displays the similar case in the similar case display region 32 of the image reading screen 30, and thus the display of the image reading screen 30 is updated (step SC16). The doctor DR views the similar case, selects the case image 20C depending on cases, and checks details after displaying the case image 20C in a full size so as to specify a disease name of a patient whose target image 20T is captured on the basis of the disease name of the similar case.

As mentioned above, since a similar case is acquired from the similar case search function unit 60, and the similar case is provided to be viewed by the doctor DR, a disease name is easily specified.

The doctor DR enters findings and the specified disease name to the entry box 40 and the entry box 41, respectively, and selects the fixed preservation button 42. Consequently, an evaluation request for the disease name entered to the entry box 41 is transmitted to the diagnosis support server 17.

Figure 26:
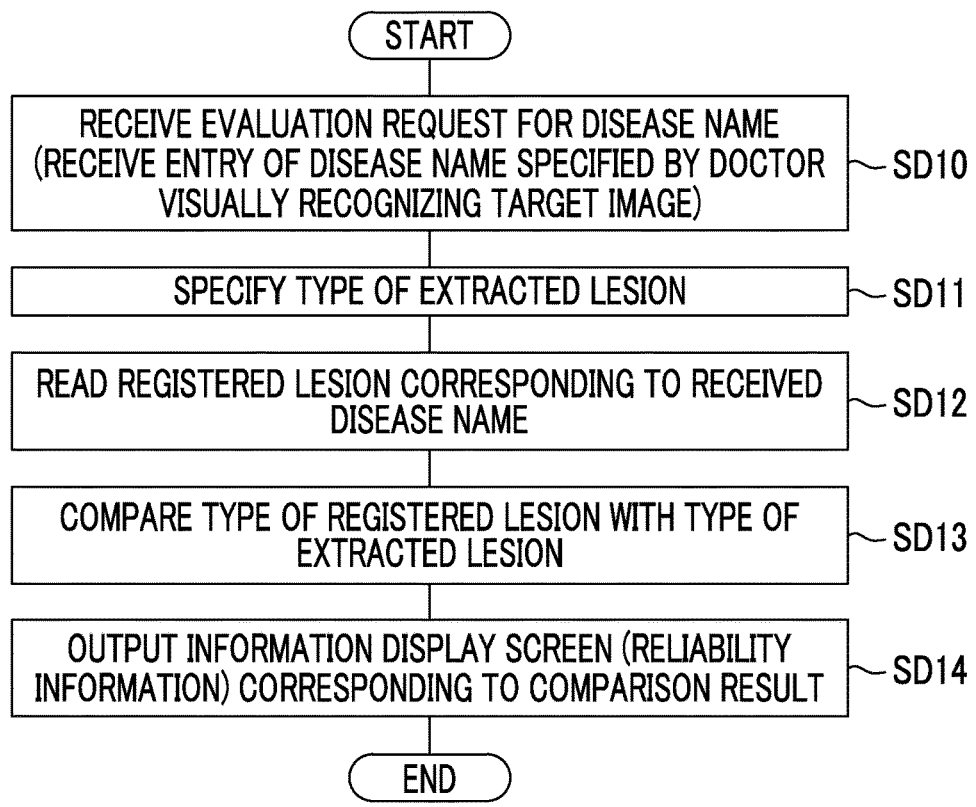
FIG. 26 is a flowchart illustrating process procedures in the diagnosis support function unit.

In FIG. 26 illustrating process procedures in the diagnosis support function unit 61, as shown in step SD10, in the diagnosis support server 17, an evaluation request for a disease name from the medical care department terminal 12 is received by the evaluation request reception portion 75 (reception step). The evaluation request for a disease name is output from the evaluation request reception portion 75 to the second image analysis portion 76 and the comparison portion 78.

The second image analysis portion 76 performs image analysis on the entire region of the target image 20T included in the evaluation request for a disease name so as to extract an extracted lesion as illustrated on the right part in FIG. 12. The type of extracted lesion is specified in the process of the extraction (step SD11; type acquisition step). The extraction result of the extracted lesion is output from the second image analysis portion 76 to the comparison portion 78.

A reading instruction for a registered lesion corresponding to the disease name included in the evaluation request is output from the comparison portion 78 to the information management portion 77 along with the image analysis in the second image analysis portion 76. Consequently, a registered lesion corresponding to the reading instruction is read from the registered lesion information 56 (step SD12; information management step). The registered lesion is output from the information management portion 77 to the comparison portion 78.

As illustrated in FIGS. 13 to 16, the comparison portion 78 compares the type of registered lesion read by the information management portion 77 with the type of extracted lesion specified by the second image analysis portion 76 (step SD13; comparison step). A comparison result is output from the comparison portion 78 to the screen output control portion 80.

The screen output control portion 80 outputs the information display screen 90 on which the reliability information 91 corresponding to the comparison result is displayed, to the medical care department terminal 12 having transmitted the evaluation request for the disease name (step SD14; output control step). More specifically, in a case where the comparison result is the first comparison result, the information display screen 90A illustrated in FIG. 18 is output, in a case where the comparison result is the second comparison result, the information display screen 90B illustrated in FIG. 20 is output, and, in a case where the comparison result is the third comparison result, the information display screen 90C illustrated in FIG. 23 is output.

The information display screen 90A displays a message indicating that the type of registered lesion matches the type of extracted lesion, and the reliability information 91 of "reliability: high" is displayed. Through such display, the doctor DR can recognize that the reliability of the specified disease name is high since the lesion referred to in specifying the disease name matches the registered lesion corresponding to the specified disease name.

The information display screen 90B displays a message indicating that there is the non-reference lesion which is present in extracted lesions but is not present in registered lesions, and the reliability information 91 of "reliability: low". Through such display, the doctor DR can recognize that the reliability of the specified disease name is low since there is the lesion not referred to in specifying the disease name.

The information display screen 90C displays a message indicating that there is the non-extracted lesion which is present in registered lesions but is not present in extracted lesions, and the reliability information 91 of "reliability: middle". Through such display, the doctor DR can recognize that the reliability of the specified disease name is middle since there is the lesion which is misrecognized in specifying the disease name, or which cannot be extracted in terms of extraction performance of the second image analysis portion 76.

The doctor DR views the information display screen 90, and determines whether to maintain the fixed preservation or to correct the disease name after returning to the image reading screen 30. In a case where the fixed preservation is maintained, the OK button 92 is selected, and, in a case where the disease name is corrected after returning to the image reading screen 30, the back button 93 (in cases of the information display screens 90A and 90C) or the link 94 (in a case of the information display screen 90B) is selected. In a case where the OK button 92 is selected, the display of the information display screen 90 and the image reading screen 30 disappears, and the image reading report information is fixedly preserved. In a case where the back button 93 or the link 94 is selected, the display of the information display screen 90 disappears, and returns to the display of the image reading screen 30.

In a case where the link 94 is selected, as illustrated in FIG. 22, the image reading screen 30 on which the target image 20T in which the non-reference lesion is present is displayed is output from the screen output control portion 80. The doctor DR checks the non-reference lesion, and corrects the disease name entered to the entry box 41 to the disease name for which the non-reference lesion is also referred to.

As mentioned above, since the comparison portion 78 compares the type of extracted lesion extracted and specified by the second image analysis portion 76 with the type of registered lesion read by the information management portion 77 and corresponding to a disease name specified by the doctor DR, and the information display screen 90 having the reliability information 91 indicating the reliability of the disease name specified by the doctor DR is output on the basis of a result of the comparison, the doctor DR can easily understand to what extent the disease name specified thereby has the reliability. The doctor DR makes an effort to correct a disease name in order to increase the reliability in cases (information display screens 90B and 90C) other than a case where high reliability is displayed (information display screen 90A). Therefore, it is possible to ensure the reliability of the disease name specified by the doctor DR.

In JP3085724B, a visually recognized lesion which is visually recognized by the doctor DR and for which findings are described in an image reading report is compared with an extracted lesion, and an overlooked lesion which is overlooked by the doctor DR is displayed for warning. Thus, there is only an effect of preventing an overlooked lesion. In contrast, in the present invention, a registered lesion corresponding to a disease name specified by the doctor DR is compared with an extracted lesion, and the reliability information 91 associated with a comparison result is output. Therefore, it is possible to provide active support to an image reading process of the doctor DR of specifying a disease name on the basis of a visually recognized lesion.

If the doctor DR has only to perform the same image reading work as in the related art of specifying a disease name on the basis of a lesion which is visually recognized by the doctor DR and of which the type is specified, the reliability information 91 can be obtained, and thus there are no unnecessary time and effort for the doctor DR to describe findings of all visually recognized lesions by hand in order to provide the lesion to comparison with an extracted lesion as in JP3085724B. Particularly, since lesions are present in a wide range in a diffuse disease, actually, it is considerably hard to describe findings of all lesions in manual work by hand, but, according to the present invention, even in a case of the diffuse disease, the time and effort are not required. Therefore, it is possible to perform diagnosis support without putting a burden on the doctor DR. It is possible to efficiently perform image reading work.

Particularly, in the present embodiment, in a case where fixed preservation button 42 is selected, an evaluation request for a disease name is transmitted from the medical care department terminal 12 to the diagnosis support server 17. Thus, there is no change in a series of image reading work of the related art in which the target image 20T is viewed, and results of visually recognizing a target lesion are entered as findings and a disease name, and image reading is completed by selecting the fixed preservation button 42. Therefore, the doctor DR has only to perform the exactly same accustomed image reading work as in the related art, and thus does not feel unnecessary stress. Of course, a dedicated button for transmitting an evaluation request for a disease name may be provided separately from the fixed preservation button 42.

In a case where a comparison result is the second comparison result, and there is a non-reference lesion, a warning indicating that the non-reference lesion is not referred to in specifying a disease name is output as the reliability information 91 as in the information display screen 90B, and thus there is a high possibility that the doctor DR may correct the disease name by referring to all target lesions including the non-reference lesion, so that the reliability of the disease name can be further ensured.

In a case where a comparison result is the third comparison result, and there is a non-extracted lesion, a warning indicating that there is the non-extracted lesion is output as the reliability information 91 as in the information display screen 90C, and thus the doctor DR can have a chance to correct a disease name by checking the non-extracted lesion again.

In the information display screen 90B, since the link 94 for displaying the target image 20T in which a non-reference lesion is present is provided, and the link 94 is selected so that the image reading screen 30 displaying the target image 20T in which the non-reference lesion is present is displayed is output, in a case where the target image 20T is a set of a plurality of examination images 20 such as tomographic images, it is possible to reduce the time and effort for the doctor DR to find the target image 20T in which the non-reference lesion is present from among the plurality of images. Since a non-reference lesion and other lesions are displayed in different aspects, the doctor DR can discriminate the non-reference lesion therefrom at a glance, and can thus smoothly perform the subsequent image reading work such as correction of a disease name.

Since the information display screen 90A is output in a case where the reliability of a disease name specified by the doctor DR is high, it is not necessary to present the information display screen 90A to the doctor DR intentionally. Thus, the information display screen 90A may not be output in a case of the first comparison result, and the information display screens 90B and 90C may be output only in a case of the second and third comparison results. There may be a configuration of outputting only the information display screen 90B which is considered to be required to be presented to the doctor DR since the reliability of a disease name specified by the doctor DR.

A display method of the reliability information 91 is not limited to three stages such as high, middle, and low exemplified above, may be two stages such as high and low, and may be three or more stages. The reliability information 91 may be represented by a numerical value such as the reliability of 100%. In the information display screen 90B, in addition to or instead of the type of non-reference lesion and the link 94 for the target image 20T in which the non-reference lesion is present, a position of the non-reference lesion such as a right upper lobe may be displayed.

Second Embodiment

Figure 27:
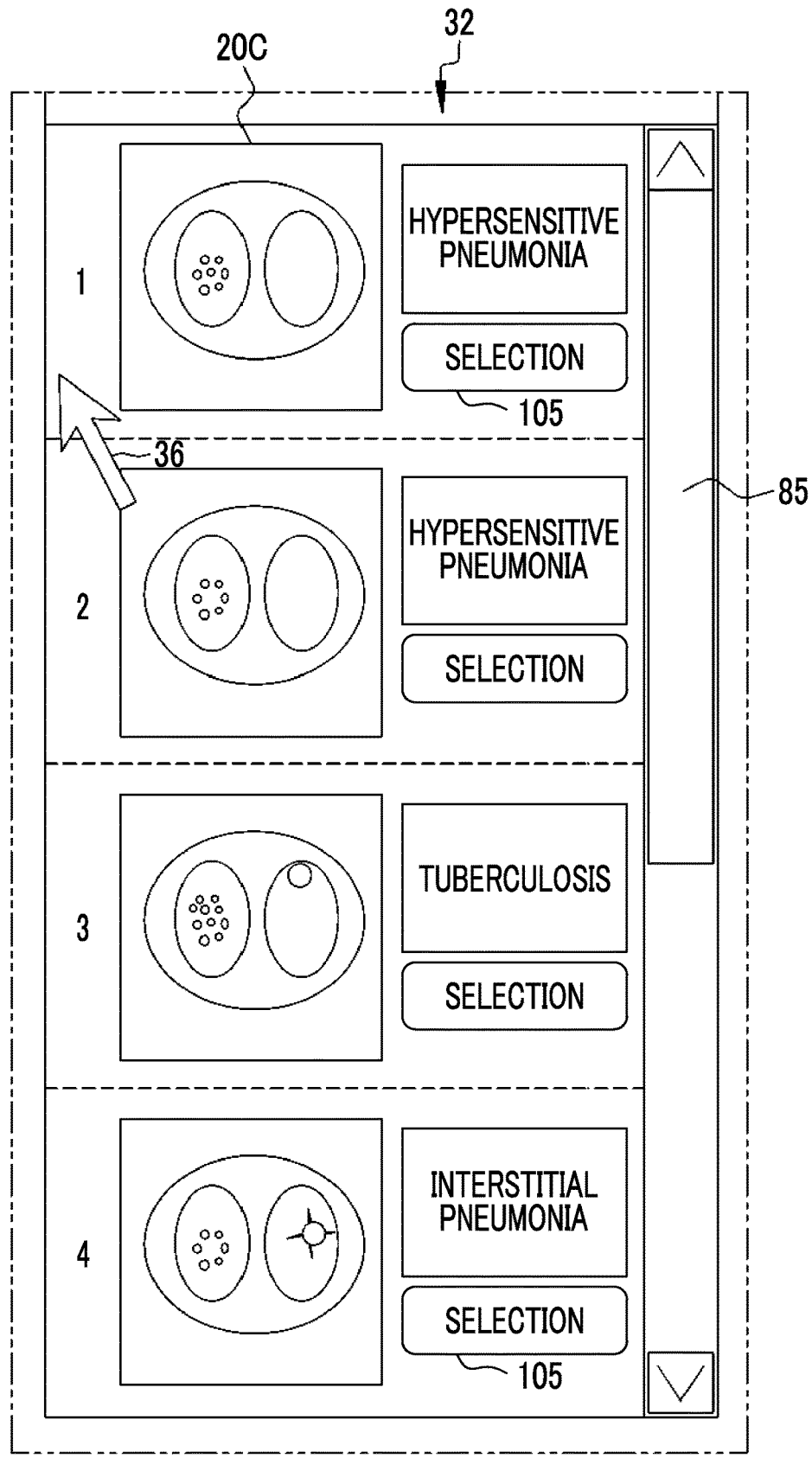
FIG. 27 is a diagram illustrating a similar case display region in which a selection button is provided.
Figure 28:
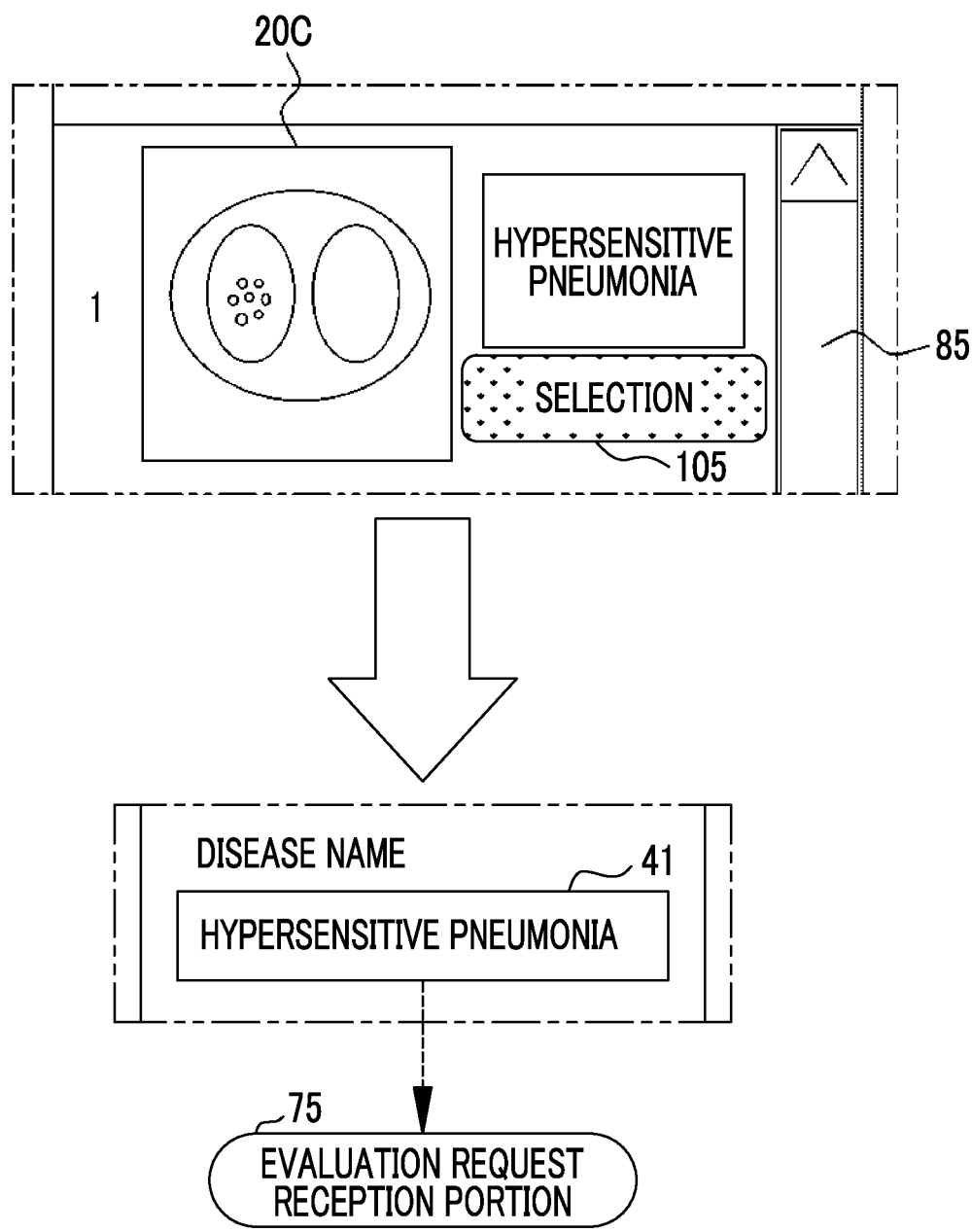
FIG. 28 is a diagram illustrating a state in which a disease name of a similar case is automatically entered to an entry box.

In the first embodiment, a disease name which is manually entered to the entry box 41 by the doctor DR is received as a disease name specified by the doctor DR, but, in the second embodiment illustrated in FIGS. 27 and 28, a disease name included in a similar case is received as a disease name specified by the doctor DR.

In FIG. 27, in the second embodiment, not only the case image 20C and a disease name of the first embodiment but also a selection button 105 is provided at each similar case displayed on the lower part in the similar case display region 32 of the image reading screen 30. The selection button 105 is a button for receiving selection of one of respective similar cases. In other words, the image reading screen 30 in this case corresponds to a similar case selection screen for receiving selection of one of the similar cases.

As illustrated in FIG. 28, if the selection button 105 is selected with the cursor 36, a disease name of a similar case corresponding to the selected selection button 105 is automatically entered to the entry box 41. If the fixed preservation button 42 is selected in this state, a disease name included in the similar case for which the selection button 105 is selected is received by the evaluation request reception portion 75 as a disease name specified by the doctor DR. Of course, in the same manner as in the first embodiment, a disease name may be manually entered to the entry box 41. FIG. 28 illustrates an example in which the selection button 105 for a similar case of hypersensitive pneumonia is selected as indicated by hatching, and the hypersensitive pneumonia is automatically entered to the entry box 41.

As mentioned above, a disease name included in a similar case for which the selection button 105 is selected is received as a disease name specified by the doctor DR, and thus the doctor DR can reduce the time and effort to manually enter a disease name. Referring to a disease name of a similar case by searching for a similar case when the doctor DR specifies a disease name is also performed in the related art, and thus the doctor DR can enter a disease name in a natural flow according to image reading work of the related art. Therefore, unnecessary stress is not applied to the doctor DR.

The selection button 105 may be provided on a full-size display screen of the case image 20C instead of the similar case display region 32. The case image 20C or a disease name in the similar case display region 32 may function as the selection button 105.

Not only the function of selecting one of respective similar cases but also the function of the fixed preservation button 42 may be added to the selection button 105. In this case, if the selection button 105 is selected, an evaluation request for a disease name of a similar case corresponding to the selected selection button 105 is immediately transmitted to the diagnosis support server 17 from the medical care department terminal 12.

Third Embodiment

The first embodiment uses the registered lesion information 56 which is created on the basis of all the cases 22 stored in the case DB 23, but, in the third embodiment illustrated in FIGS. 29 to 37, registered lesion information is updated on the basis of a disease name included in a similar case and the type of case lesion, and updated registered lesion information is used.

Figure 29:
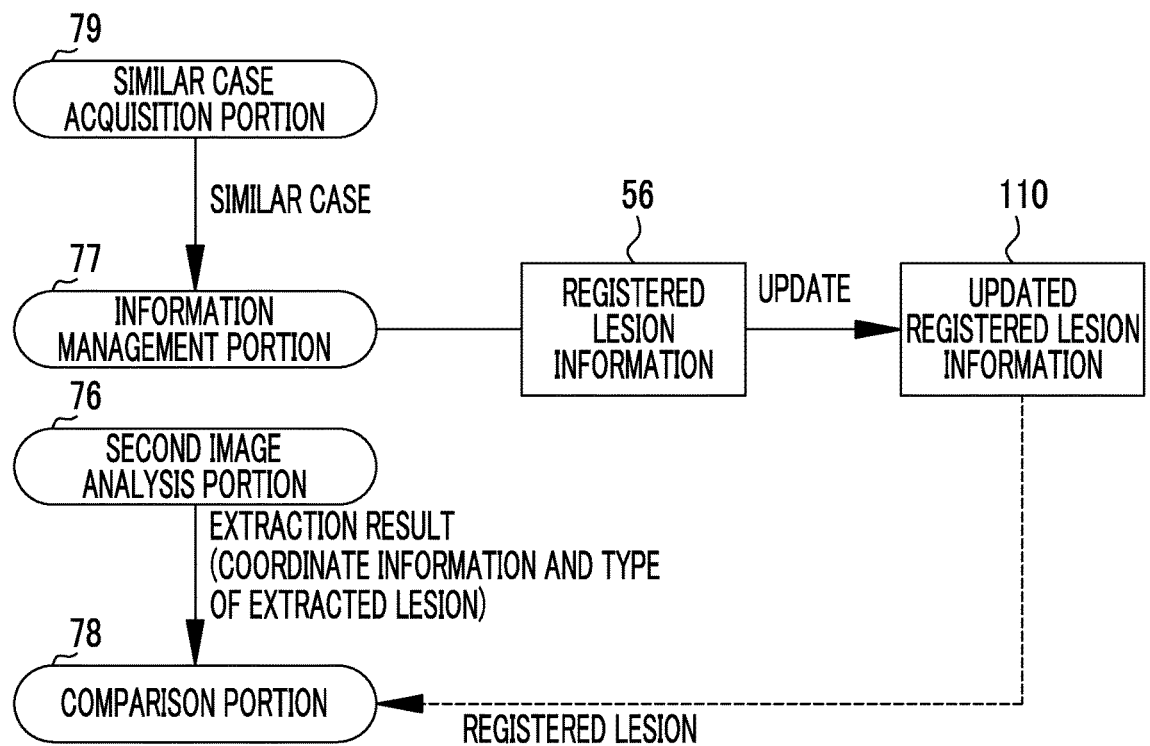
FIG. 29 is a block diagram illustrating a third embodiment of updating registered lesion information on the basis of a similar case.

As illustrated in FIG. 29, in the third embodiment, the similar case acquisition portion 79 outputs a similar case to the information management portion 77. The information management portion 77 updates the registered lesion information 56 to updated registered lesion information 110 on the basis of a disease name included in the similar case and the type of case lesion from the similar case acquisition portion 79. The comparison portion 78 compares the type of registered lesion read from the updated registered lesion information 110 by the information management portion 77 with the type of extracted lesion specified by the second image analysis portion 76.

Figure 30:
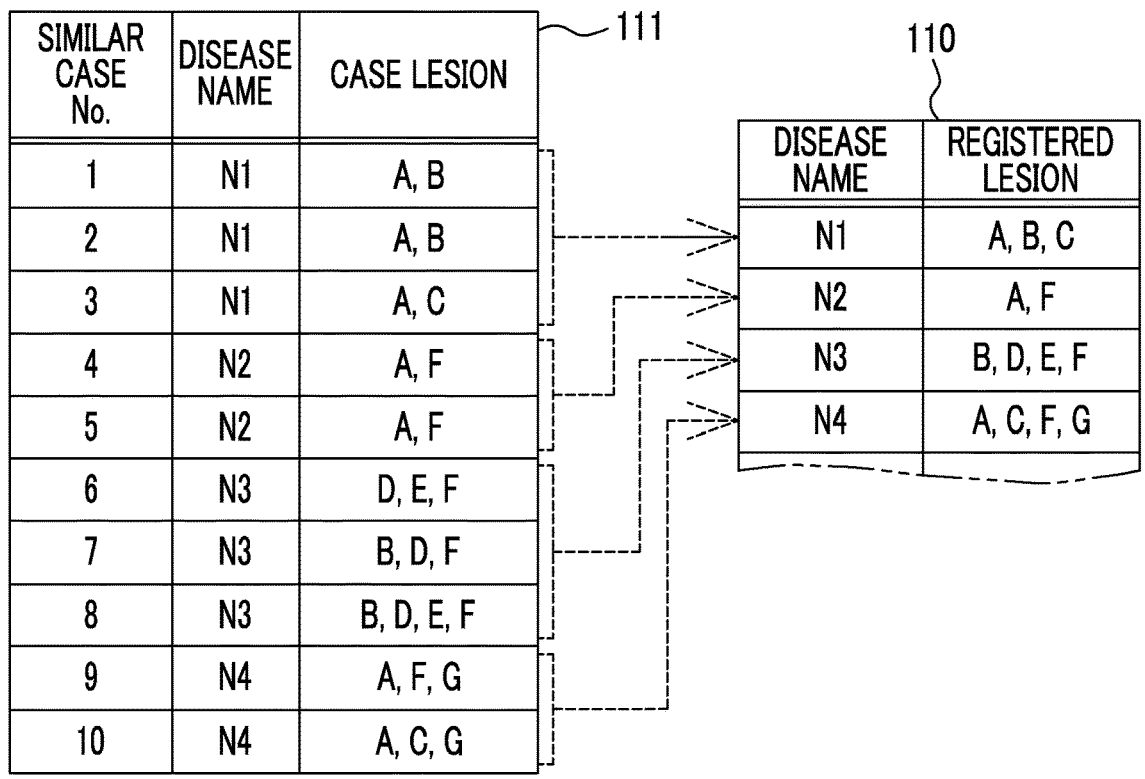
FIG. 30 is a diagram for explaining a state in which the registered lesion information is updated.

As an example, a case is assumed in which similar cases are No. 1 to No. 10 in a table 111 illustrated in FIG. 30. In this case, since the types of case lesions of similar cases having a disease name N1 of No. 1 to No. 3 are A and B for No. 1 and No. 2 and A and C for No. 3, and are thus arranged into A, B, and C, the information management portion 77 registers A, B, and C as registered lesions of the disease name N1 of the updated registered lesion information 110. In the same manner for disease names N2, N3 and N4, the information management portion 77 registers A and F as registered lesions of the disease name N2, registers B, D, E and F as registered lesions of the disease name N3, and registers A, C, F and G as registered lesions of the disease name N4.

Case lesions of disease names other than the disease names mentioned in the similar cases are not known naturally, and thus the information management portion 77 does not update registered lesions of disease names other than the disease names mentioned in the similar cases, and maintains the registered lesion information 56. Thus, in the registered lesion information 56, registered lesions of all disease names are not updated, and only registered lesions of disease names mentioned in similar cases are updated. In FIG. 30, registered lesions of disease names other than the disease names N1 to N4 mentioned in the similar cases are not updated.

Figure 31:
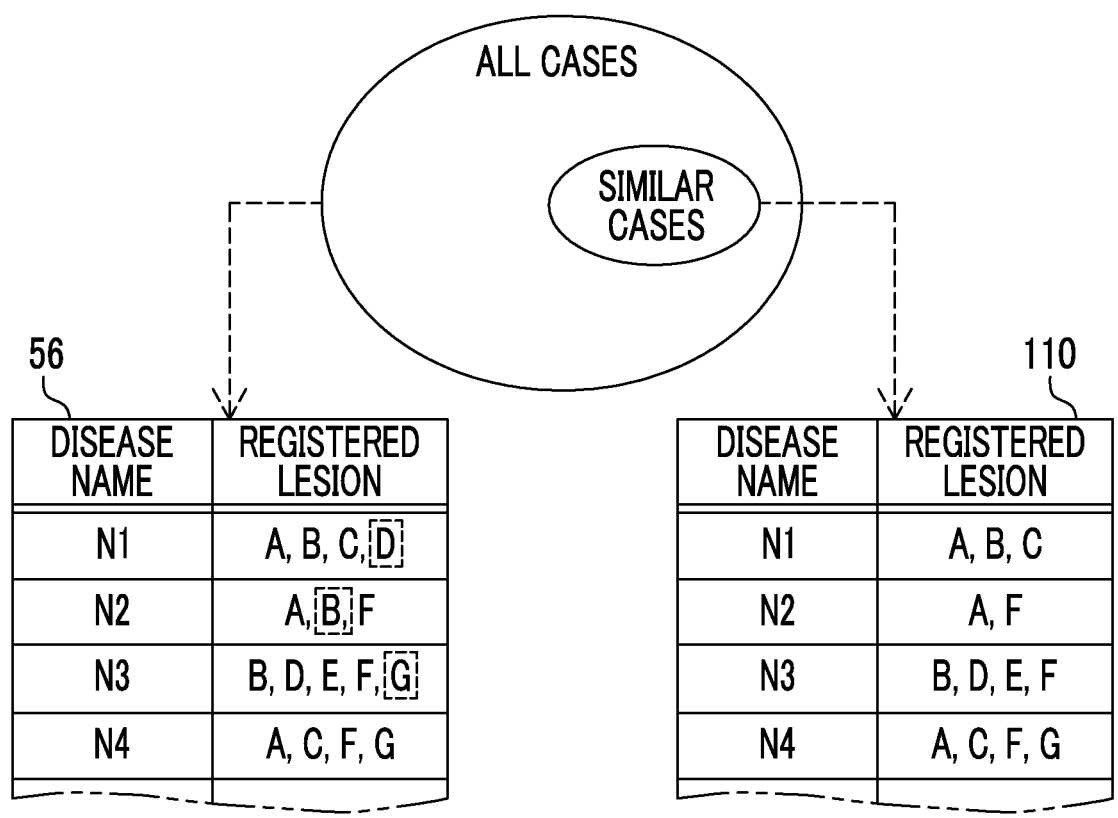
FIG. 31 is a diagram illustrating registered lesion information based on all cases and updated registered lesion information based on similar cases.

As illustrated in FIG. 31, in the registered lesion information 56 created on the basis of all the cases 22, all of the cases 22 are targets, and thus a lesion having relatively weak relevance with a disease name as in the case 22 of a rare case in a certain disease, may also be registered. In contrast, in the updated registered lesion information 110, registered lesions are narrowed into only case lesions of similar cases, and thus the number of types of registered lesions is generally reduced.

Figure 32:
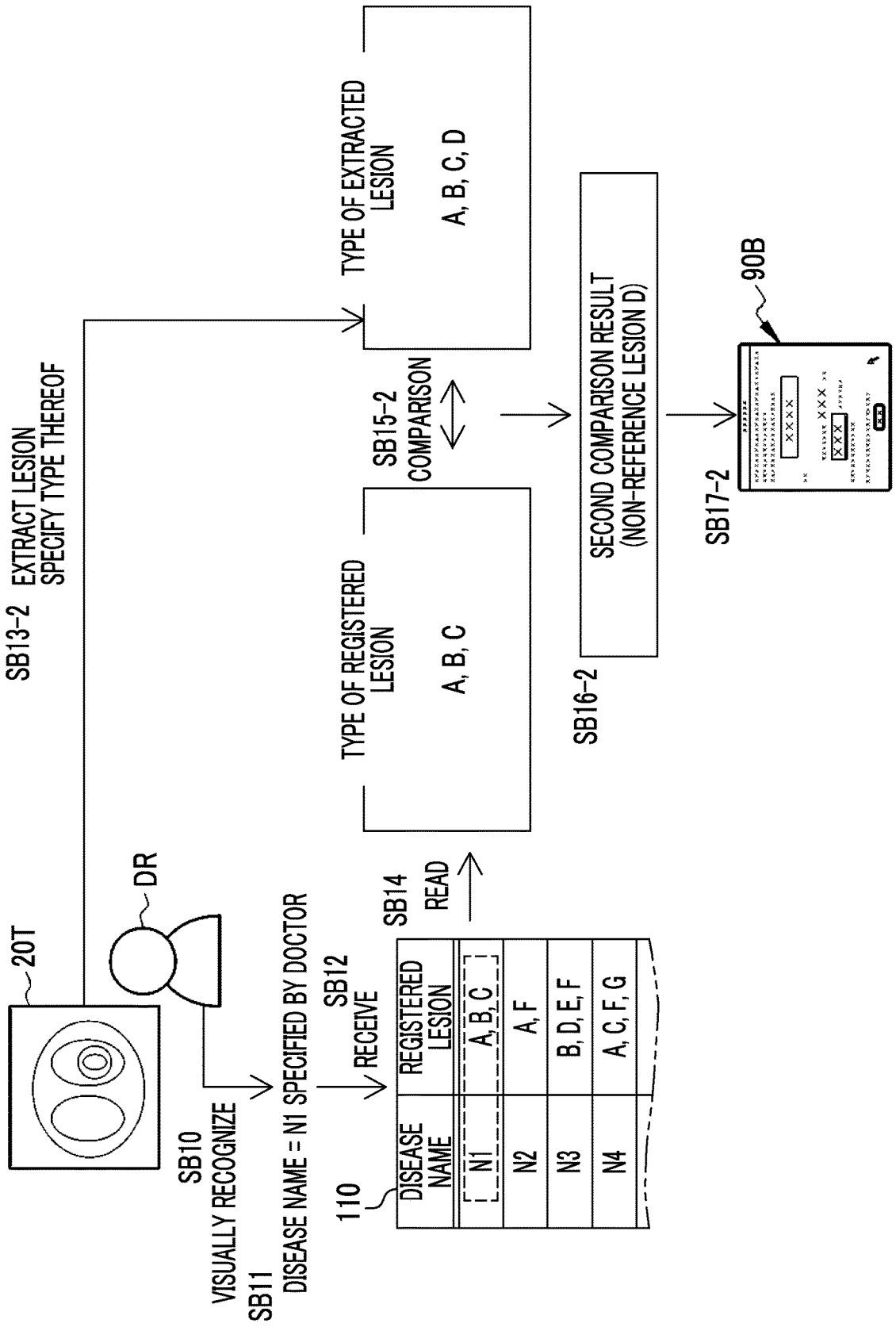
FIG. 32 is a diagram for explaining a flow until an information display screen is output in a case where the updated registered lesion information is used.

Thus, for example, in a case where a disease name specified by the doctor DR is N1, and extracted lesions are A, B, C, and D, according to the registered lesion information 56, since the registered lesions A, B, C and D are the same as the extracted lesions A, B, C and D, as illustrated in FIG. 19, the first comparison result is obtained, and thus the information display screen 90A is output. However, according to the updated registered lesion information 110, as illustrated in FIG. 32, since the extracted lesions A, B, C and D are more than the registered lesions A, B and C, and thus a non-reference lesion is the lesion D, the second comparison result is obtained. Therefore, the information display screen 90B on which the reliability information 91 of "reliability: low" is displayed is output. Consequently, the doctor DR can be made to reconsider a probability of disease names other than the disease name N1, and thus it is possible to further ensure the reliability of a disease name.

Figure 33:
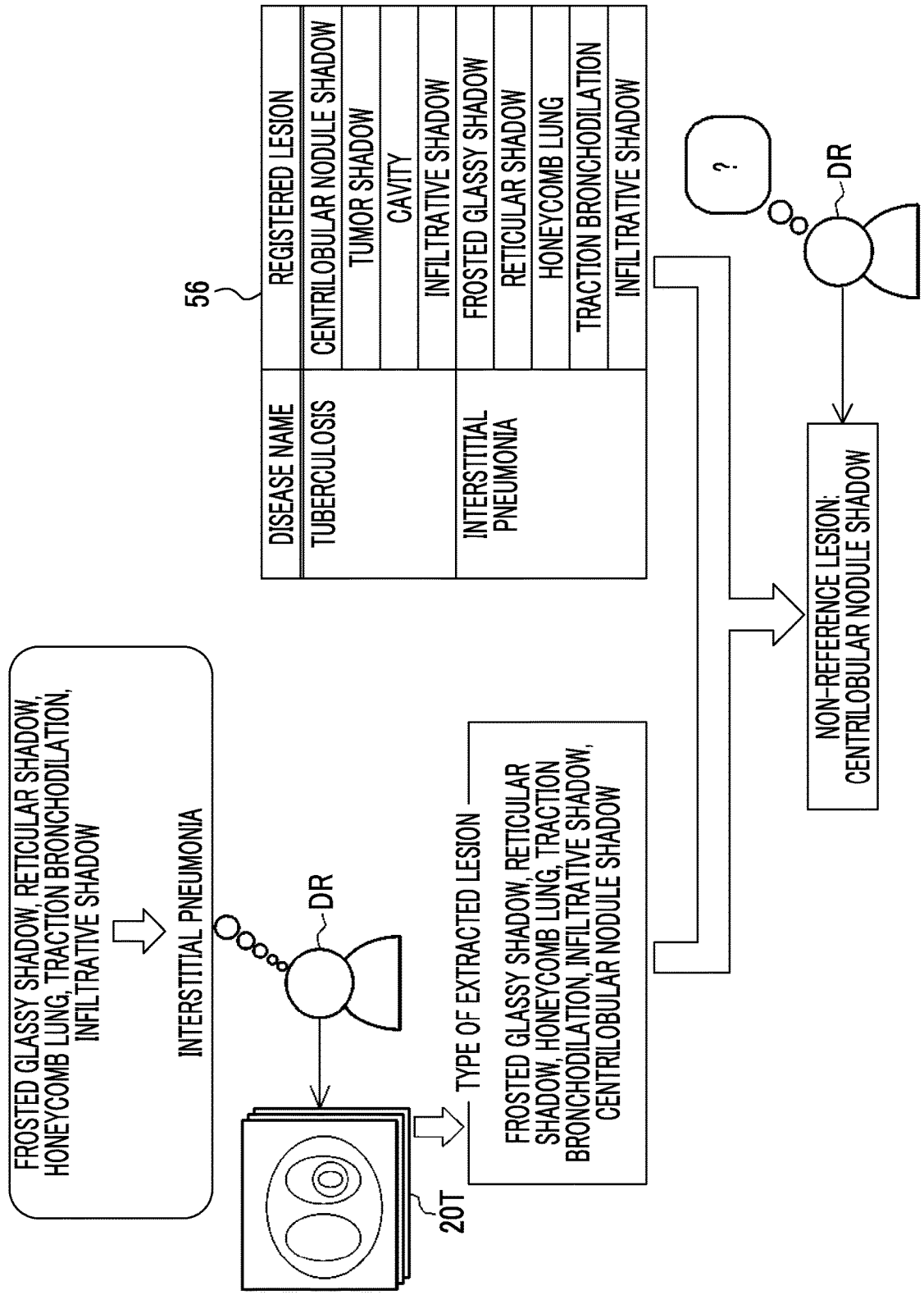
FIG. 33 is a diagram illustrating a specific example of a case of using the registered lesion information.
Figure 34:
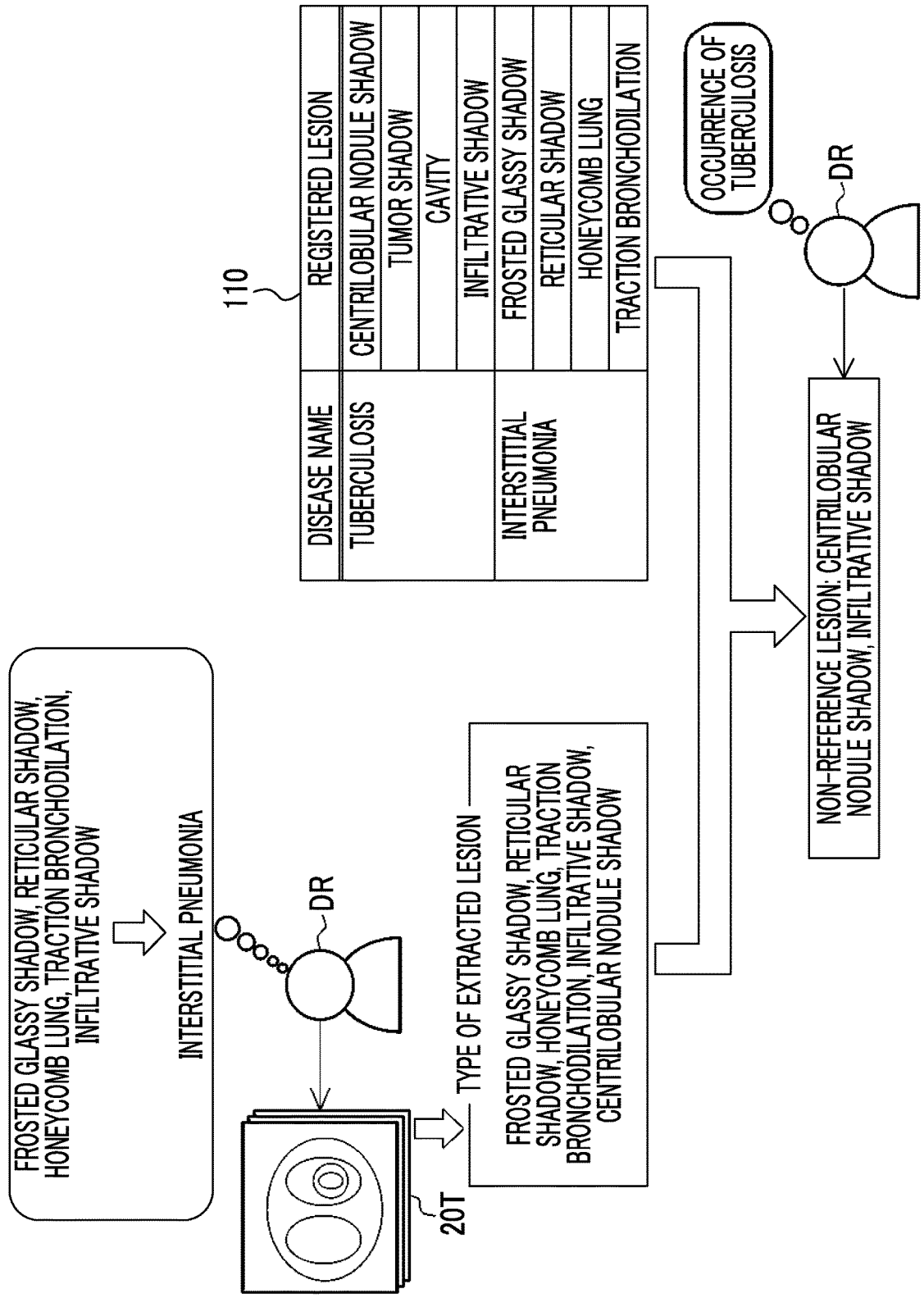
FIG. 34 is a diagram illustrating a specific example of a case of using the updated registered lesion information.

FIGS. 33 and 34 illustrate more specific examples. FIG. 33 illustrates a case of using the registered lesion information 56, and FIG. 34 illustrates a case of using the updated registered lesion information 110. Both of FIGS. 33 and 34 illustrate a case where the doctor DR visually recognizes a total of five types of target lesions such as a frosted glassy shadow, a reticular shadow, a honeycomb lung, traction bronchodilation, and an infiltrative shadow from the target image 20T, and specifies a disease name as interstitial pneumonia, and the second image analysis portion 76 extracts a centrilobular nodule shadow as an extracted lesion in addition to the five types. The centrilobular nodule shadow is a target lesion which is overlooked or intentionally ignored by the doctor DR.

In FIG. 33, registered lesions of interstitial pneumonia are five types of a frosted glassy shadow, a reticular shadow, a honeycomb lung, traction bronchodilation, and an infiltrative shadow as illustrated in FIG. 9. Thus, only the centrilobular nodule shadow is displayed on the information display screen 90B as a non-reference lesion.

The display of only the centrilobular nodule shadow is not sufficient as a hint to cause the doctor DR to reconsider disease names other than the interstitial pneumonia. The doctor DR does not reconsider that the five types of target lesions are caused by diseases other than the interstitial pneumonia due to a prejudice that the target lesions visually recognized by the doctor DR are caused by the interstitial pneumonia. This is even more in a case where the doctor DR intentionally ignores the centrilobular nodule shadow.

In contrast, in FIG. 34, registered lesions of the interstitial pneumonia are four types, that is, a frosted glassy shadow, a reticular shadow, a honeycomb lung, and traction bronchodilation except for an infiltrative shadow. Thus, the infiltrative shadow is displayed on the information display screen 90B in addition to the centrilobular nodule shadow as non-reference lesions.

In this case, initially, the doctor DR regards the infiltrative shadow to be caused by the interstitial pneumonia, overlooks or ignores the centrilobular nodule shadow, and specifies the interstitial pneumonia as a disease name. However, if the information display screen 90B presenting the centrilobular nodule shadow and the infiltrative shadow as non-reference lesions is displayed, the doctor DR can be aware that the infiltrative shadow is caused by diseases other than the interstitial pneumonia on the basis of a pair of the centrilobular nodule shadow and the infiltrative shadow, and can thus judge, for example, the concurrence of tuberculosis.

As mentioned above, by using the updated registered lesion information 110 which is updated on the basis of a disease name included in a similar case and the type of case lesion, a target lesion which is disregarded in a case of using the registered lesion information 56 created on the basis of all of the cases 22 can be mentioned as a non-reference lesion, and thus the doctor DR can have a chance to reconsider a probability of disease names other than an initially specified disease name.

It may be determined whether or not a case lesion is registered in the updated registered lesion information 110 as a registered lesion according to the number of case lesions of the same type appearing in similar cases of the same disease. For example, a condition is set in which, in a case where the number of case lesions is two or more, the case lesion is registered in the updated registered lesion information 110 as a registered lesion. In this case, when described by exemplifying the table 111 in FIG. 30, since the number of case lesions A appearing in the disease name N1 is three, the number of case lesions B is two, and the number of case lesion C is one, the case lesions A and B whose number is two or more are registered in the updated registered lesion information 110 as registered lesions, and the case lesion C whose number is one is not registered in the updated registered lesion information 110. In the above-described way, registered lesions can be further narrowed.

Figure 36:
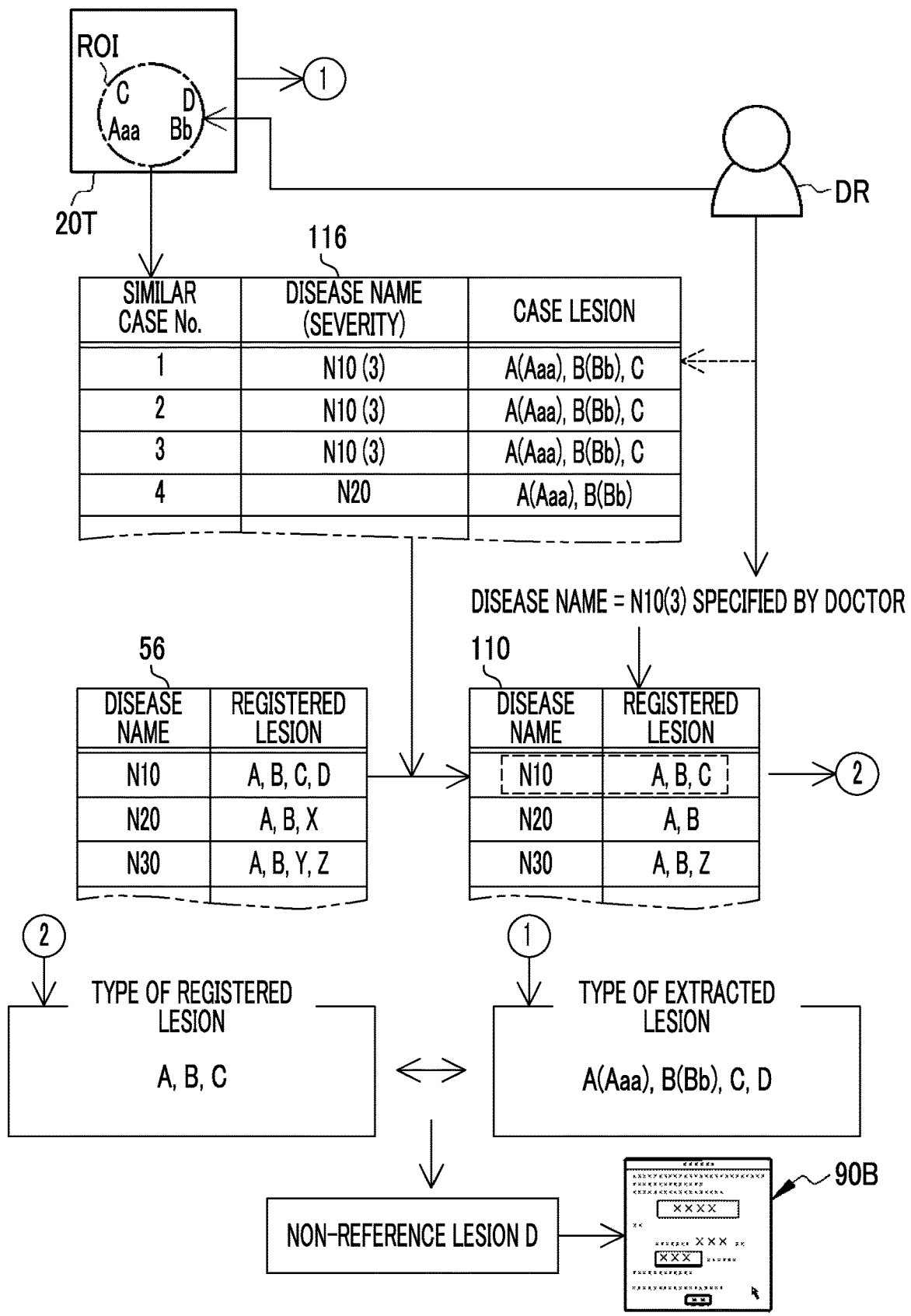
FIG. 36 is a diagram for explaining an effect in a case of using the updated registered lesion information.
Figure 37:
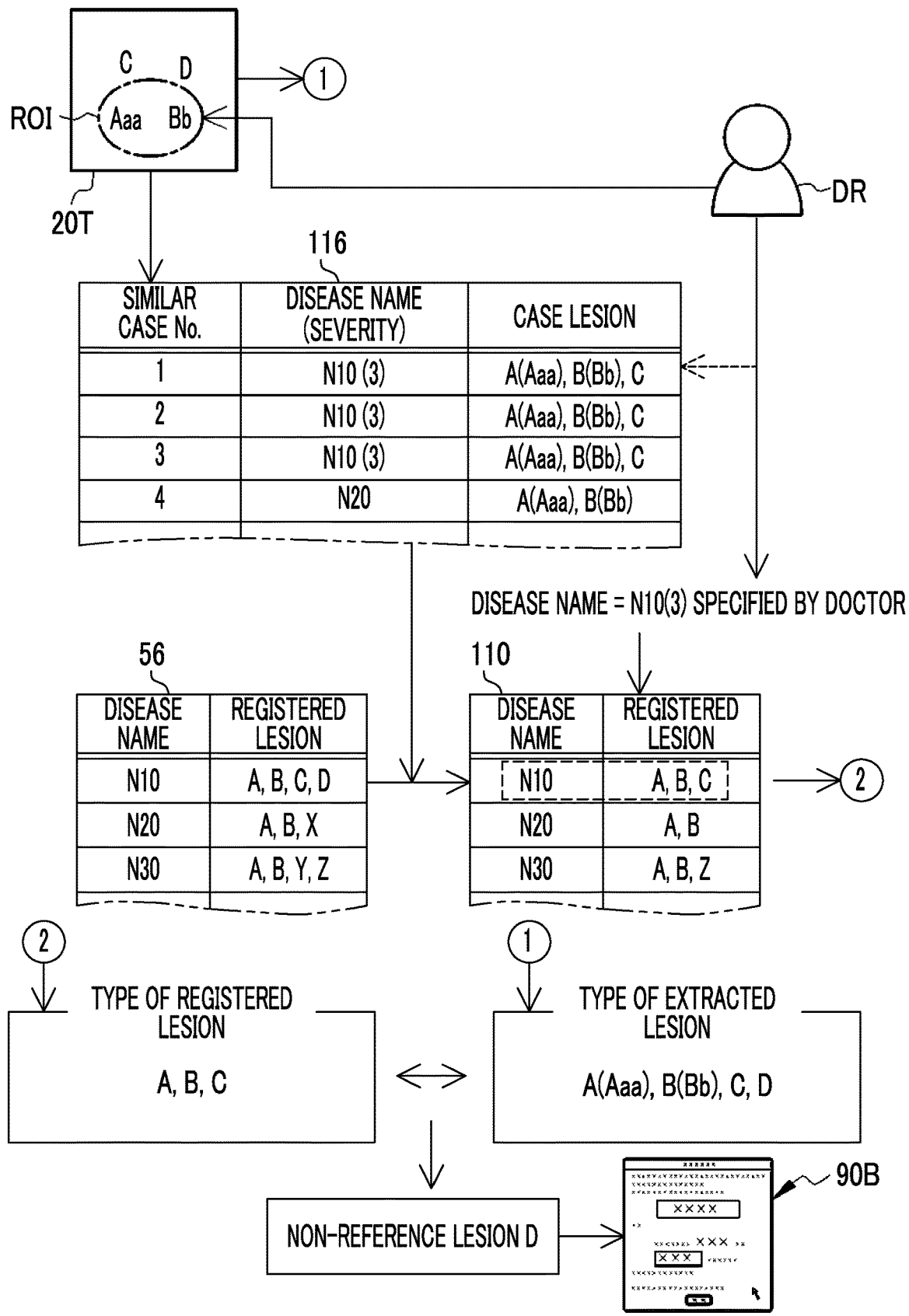
FIG. 37 is a diagram for explaining an effect in a case of using the updated registered lesion information.

With reference to FIGS. 35 to 37, a description will be made of effects achieved by using the updated registered lesion information 110 instead of the registered lesion information 56.

In image reading, the severity of a disease may be specified along with a disease name. The severity is expressed stepwise in stages such as slight, moderate, and serious, or a first stage and a second stage. The severity and the type of lesion have a correspondence relationship in the same manner as in a disease. For example, there is a state in which a lesion is a single type in a case where the severity is slight, and increases to four types in a case where the severity is serious.

Here, as shown in a table 115 in FIG. 35, a there is assumed to be a disease N10 for which a lesion changes depending on the severity such as a lesion A in a case of the severity 1 and lesions Aa and B in a case of the severity 2. Uppercase alphabets such as A, Aa, Aaa, and Aaaa are different from each other in terms of a size, the number, a density, or the like, and are lesions of the same type.

As illustrated in FIG. 36, a case is assumed in which the doctor DR visually recognizes the target image 20T in which target lesions Aaa, Bb, C and D are present, a region including the target lesions Aaa, Bb, C and D is designated as the region of interest ROI, similar cases are searched for by using the target lesions Aaa, Bb, C and D as reference lesions so that similar cases shown in a table 116 are searched for, and thus the doctor DR specifies N10 as a disease name and 3 as the severity.

In this case, since the lesions Aaa, Bb and C are present in reference lesions in the region of interest ROI, as shown in the table 116, there is a case where, as similar cases, the case 22 of the disease name N10 having the case lesions Aaa, Bb and C and the severity 3 is searched for instead of the case 22 of the disease name N10 having the case lesions Aaaa, Bbb, Cc and D and the severity 4. Thus, the information management portion 77 updates the registered lesion information 56 in the registered lesions A, B, C and D of the disease name N10 to A, B, and C as the updated registered lesion information 110.

Therefore, registered lesions of the disease name N10 specified by the doctor DR are A, B, and C according to the updated registered lesion information 110. On the other hand, the types of extracted lesions specified by the second image analysis portion 76 are naturally A(Aaa), B(Bb), C, and D. Thus, a comparison result is the second comparison result, and the lesion D is displayed on the information display screen 90B as a non-reference lesion.

In a case of using the registered lesion information 56, the lesion D is included in the registered lesions of the disease name N10, and thus the lesion D is not displayed as a non-reference lesion. In contrast, if the updated registered lesion information 110 is displayed, the lesion D can be displayed as a non-reference lesion. Thus, the doctor DR specifies N10 as a disease name and 3 as the severity since, among the target lesions Aaa, Bb, C and D which are initially visually recognized and are designated as the region of interest ROI, the target lesions Aaa, Bb and C correspond to the severity 3 of the disease N10 in the table 115, and the cases 22 of the severity 3 of the disease N10 are searched for as similar cases. However, the lesion D which is initially visually recognized and is designated as the region of interest ROI is displayed as a non-reference lesion, and thus the doctor DR can be aware of whether the lesion D is caused by diseases other than the disease N10.

FIG. 37 illustrates a case where, among the target lesions Aaa, Bb, C and D, a region including the target lesions Aaa and Bb is designated as the region of interest ROI. The remaining is the same as in FIG. 36. In this case, since the lesion D which is not expected in the disease name N10 and the severity 3 specified on the basis of the target lesions Aaa and Bb and the similar cases is displayed as a non-reference lesion, the doctor DR can be aware of whether the lesion D is caused by diseases other than the disease N10 in the same manner as in the case of FIG. 36.

Fourth Embodiment

As described in FIG. 31, in the registered lesion information 56 created on the basis of all the cases 22, a registered lesion which occurs in few patients with the disease, that is, of which an occurrence frequency is relatively low is mixed with a registered lesion which occurs in most patients with the disease, that is, of which an occurrence frequency is relatively high. Thus, there is a difference in the reliability of a disease name specified by the doctor DR in a case where a registered lesion whose occurrence frequency is relatively low is included in a non-reference lesion and a case where a registered lesion whose occurrence frequency is relatively high is included in a non-reference lesion. Therefore, in a fourth embodiment illustrated in FIGS. 38 to 40, an output aspect of the reliability information 91 differs depending on an occurrence frequency of a non-reference lesion.

Registered lesion information 120 illustrated in FIG. 38 is obtained by adding an item of an occurrence frequency of a registered lesion to the registered lesion information 56 illustrated in FIG. 9 of the first embodiment. The occurrence frequency is represented in percentage, and is registered for each disease name. The occurrence frequency is obtained by dividing the number of cases of a certain disease having a registered lesion as a case lesion by the total number of cases of the certain disease and multiplying a result thereof by 100. For example, in a case where the number of cases of tuberculosis having a centrilobular nodule shadow is 18, and the total number of cases of tuberculosis is 20, an occurrence frequency of the centrilobular nodule shadow of tuberculosis is (18/20)×100=90%.

Figure 39:
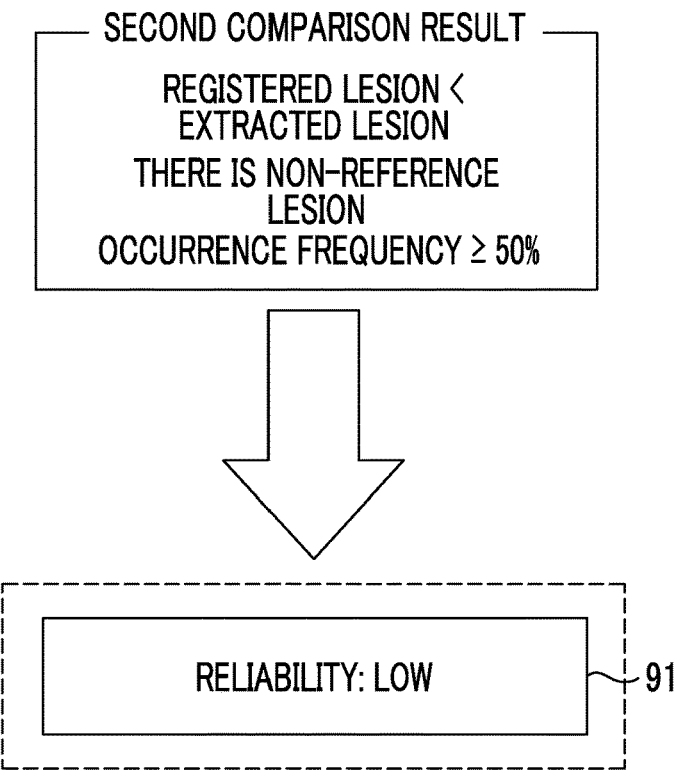
FIG. 39 is a diagram illustrating an example in which output aspects of reliability information are different from each other according to an occurrence frequency of a non-reference lesion.

As illustrated in FIG. 39, in a case where a comparison result is the second comparison result, and an occurrence frequency of a non-reference lesion is 50% or more (occurrence frequency ≥50%), "reliability: low" is recorded in the reliability information 91 of the information display screen 90B. On the other hand, as illustrated in FIG. 40, in a case where an occurrence frequency of a non-reference lesion is less than 50% (occurrence frequency <50%), "reliability: middle" is recognized in the reliability information 91.

As in FIG. 39, in a case where a registered lesion whose occurrence frequency is 50% or more and relatively high is a non-reference lesion, it is considered that the reliability of a disease name specified by the doctor DR is lower, and thus the reliability information 91 indicating that the reliability of the disease name is low is output. In contrast, as in FIG. 40, in a case where a registered lesion whose occurrence frequency is relatively low is a non-reference lesion, it is considered that the reliability of a disease name specified by the doctor DR is higher than at least in the case of FIG. 39, and thus the reliability information 91 indicating that the reliability of the disease name is middle is output.

As mentioned above, since an occurrence frequency of a registered lesion is registered in the registered lesion information 120, and an output aspect of the reliability information 91 differs depending on an occurrence frequency of a non-reference lesion, it is possible to strongly prompt the doctor DR to correct a disease name, particularly, in a case where a registered lesion whose occurrence frequency is relatively high is a non-reference lesion.

Figure 40:
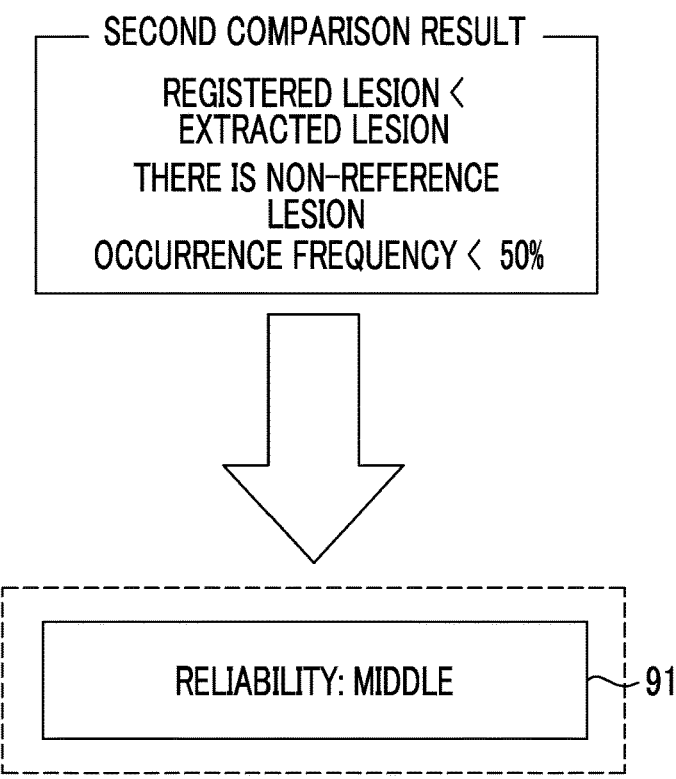
FIG. 40 is a diagram illustrating an example in which output aspects of reliability information are different from each other according to an occurrence frequency of a non-reference lesion.

An example in which an output aspect of the reliability information 91 differs depending on an occurrence frequency of a non-reference lesion is not limited to the examples illustrated in FIGS. 39 and 40. For example, in a case where an occurrence frequency of a non-reference lesion is 90% or more, "reliability: low" may be recorded in the reliability information 91, and the reliability information 91 may be displayed in a blinking manner. In a case where an occurrence frequency of a non-reference lesion is less than 10%, the information display screen 90A may be output instead of the information display screen 90B in the same manner as in a case of the first comparison result.

In FIG. 38, a description has been made of an example of the registered lesion information 120 obtained by adding the item of an occurrence frequency to the registered lesion information 56 of the first embodiment, but the item of an occurrence frequency may be added to the updated registered lesion information 110 of the third embodiment.

Fifth Embodiment

In the first embodiment, an evaluation request for a disease name is received by the evaluation request reception portion 75, and undergoes image analysis in the second image analysis portion 76 so that an extracted lesion is extracted, and the type thereof is specified, but the present invention is not limited thereto.

For example, when the target image 20T is displayed in the image display region 31 of the image reading screen 30, the target image 20T may be transmitted from the medical care department terminal 12 to the diagnosis support server 17, and extraction of an extracted lesion and specifying of the type thereof may be performed by activating the second image analysis portion 76. In this case, the screen output control portion 80 outputs an image reading screen 125 illustrated in FIG. 41, in which the extraction result of the extracted lesion in the second image analysis portion 76 is reflected.

Figure 41:
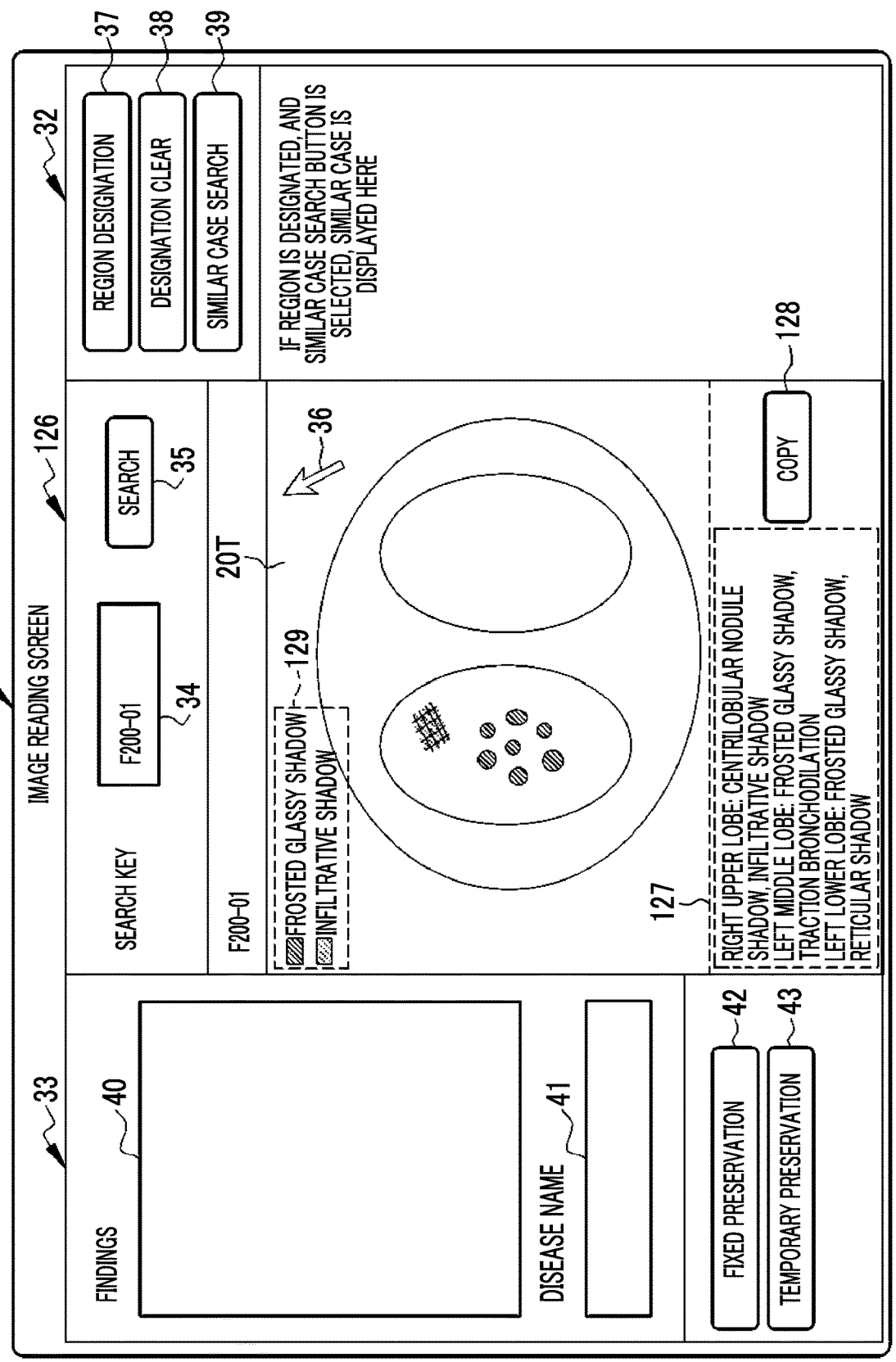
FIG. 41 is a diagram illustrating an image reading screen on which a lesion extraction result is displayed.

In FIG. 41, a fundamental configuration of the image reading screen 125 is the same as that of the image reading screen 30 illustrated in FIG. 6 in the first embodiment, but the image reading screen 125 is different from the image reading screen 30 in terms of a configuration of an image display region 126. In other words, text information 127 indicating the extraction result of the extracted lesion output from the second image analysis portion 76 is displayed on a lower part in the target image 20T in the image display region 126. The text information 127 is, specifically, a position of an extracted lesion such as a right upper lobe, and the type of extracted lesion such as a centrilobular nodule shadow.

A copy button 128 is provided on the right side of the text information 127. If the copy button 128 is selected with the cursor 36, the text information 127 is automatically entered to the findings entry box 40.

In the target image 20T, the extracted lesions are colored in different colors for the respective types thereof. A legend 129 of extracted lesions is displayed on an upper part in the target image 20T. FIG. 41 illustrates an example in which a frosted glassy shadow and a reticular shadow are colored in different colors (for example, the frosted glassy shadow is colored red, and the reticular shadow is colored green).

As mentioned above, if the image reading screen 125 in which an extraction result of an extracted lesion in the second image analysis portion 76 is reflected is output, the doctor DR can more smoothly perform image reading work. Since a probability that the doctor DR may overlook a target lesion is reduced, the out of the image reading screen 125 can be used as a double safety measure to prevent misdiagnosis along with the output of the reliability information 91.

In a case where the target image 20T is a set of a plurality of examination images 20, a scout image covering the entire imaging part may be displayed, and a mark indicating a position of an extracted lesion may be added to the scout image. For example, in a CT apparatus, the scout image is obtained by capturing a front image of a patient lying on a bed in a state in which an X-ray tube bulb is fixed at a single location before a tomographic image is captured.

Display of an extraction result of an extracted lesion such as coloring of the text information 127 or a lesion may be configured to be able to switch between display and non-display. The target image 20T in which a lesion is colored and the target image 20T in which a lesion is not colored may be displayed to be arranged on the basis of an extraction result of an extracted lesion.

Extraction of an extracted lesion and specifying of the type thereof may be performed in the second image analysis portion 76 at a timing at which the examination image 20 is stored in the examination image DB. In this case, an extraction result of an extracted lesion is stored as accessory information of the examination image 20.

In the above-described embodiments, a description has been made of an aspect in which the doctor DR designates the region of interest ROI, but image analysis may be performed on the target image 20T, and the region of interest ROI in which the presence of a target lesion is doubtful may be automatically designated.

In the above-described embodiments, a description has been made of a case where the type and the feature amount ZC of a case lesion are specified and calculated before searching for a similar case, and the case 22 including the type and the feature amount ZC of the case lesion is stored in the case DB 23, but the second image analysis portion 76 may specify the type of case lesion, and the feature amount calculation portion 68 may calculate the feature amount ZC of the case lesion in the same method as in the type of extracted lesion and the feature amount ZT of a reference lesion, whenever a similar case is searched for. In the above-described way, the type and the feature amount ZC of a case lesion are not required to be included in the case 22.

A similar case may be searched for by referring to other information such as a measurement result of a vital sign, a result of blood examination, and findings during inquiry described in an electronic medical chart.

The similar case search function unit 60 and the diagnosis support function unit 61 may be partially common to each other. For example, the search request reception portion 65 and the evaluation request reception portion 75 are integrated into a single reception portion, and, similarly, the first image analysis portion 67 and the second image analysis portion 76 are integrated into a single image analysis portion. Conversely, the screen output control portion 80 may be divided into a control portion for outputting a similar case and a control portion for outputting the reliability information 91.

In the above-described embodiments, the similar case search function unit 60 and the diagnosis support function unit 61 are built into the CPU of the diagnosis support server 17, and thus the diagnosis support server 17 functions as a similar case search apparatus and a diagnosis support apparatus, but a similar case search server which is different from the diagnosis support server 17 may have the function of the similar case search apparatus.

In the above-described embodiments, a diagnosis support apparatus of the present invention has been described in a form of the diagnosis support server 17 outputting the reliability information 91 in response to an evaluation request for a disease name from the medical care department terminal 12, but the medical care department terminal 12 may have the function of the diagnosis support apparatus. In this case, each portion of the diagnosis support function unit 61 is built into the CPU of the medical care department terminal 12. Similarly, each portion of the similar case search function unit 60 may be built into the CPU of the medical care department terminal 12, and thus the medical care department terminal 12 may have the function of the similar case search apparatus.

The examination image DB server 15, the case DB server 16, and the diagnosis support server 17 may be configured as different servers in the same manner as in the above-described embodiments, and may be integrated into a single server. Case lesion information or image reading report information may be stored in a DB server which is different from a server storing the case 22.

The diagnosis support function unit 61 of the diagnosis support server 17 may be formed of a plurality of server computers which are separate from each other as hardware in order to improve process performance or reliability. For example, the respective portions are distributed to a plurality of server computers such as a server computer having the functions of the evaluation request reception portion 75 and the second image analysis portion 76, a server computer having the functions of the information management portion 77 and the comparison portion 78, and a server computer having the functions of the similar case acquisition portion 79 and the screen output control portion 80.

As mentioned above, a hardware configuration of the communication system may be changed as appropriate according to required performance such as processing capacity, safety, and reliability. Not only hardware but also an AP such as the operation program 55 may be distributed to and stored in a plurality of storage devices in order to ensure safety or reliability.

In the above-described embodiments, the medical information system 2 built into a facility has been exemplified, and an aspect of using the diagnosis support server 17 in a single facility has been described, but there may be an aspect in which the diagnosis support server 17 may be used by a plurality of facilities.

In the above-described embodiments, the diagnosis support server 17 is an aspect of being communicably connected to a client terminal such as the medical care department terminal 12 or the like provided in a single medical facility via the network 18 such as LAN' and providing an application server such as a similar case search in response to a request from the client terminal. In order to use the diagnosis support server 17 in a plurality of medical facilities, the diagnosis support server 17 is communicably connected to each of client terminals provided in the plurality of facilities via, for example, a wide area network (WAN) such as the Internet or a public communication network. A request from each client terminal of the plurality of medical facilities is received by the diagnosis support server 17 via the WAN such as the Internet or a public communication network, and an application service of a similar case search is provided to each client terminal. In a case of using the WAN, it is preferable to build a virtual private network (VPN) or to use a communication protocol with a high security level such as Hypertext Transfer Protocol Secure (HTTPS).

An installation location and an operation body of the diagnosis support server 17 in this case may be a data center operated by a company which is different from a company operating a medical facility, and may be one of a plurality of medical facilities.

The present invention is not limited to the above-described embodiments, and may employ various configurations without departing from the spirit of the invention.

For example, one or a plurality of target images 20T may be included in a search request for a similar case. In a case of a plurality of target images, the region information 25 is added to each target image 20T. The examination image 20 may be captured not only by the CT apparatus exemplified in the above-described embodiments but also by the modality 13 such as an ultrasonic probe, an electron microscope, or a mammography apparatus.

In the above-described embodiments, a search request for a similar case including the entire target image 20T and the region information 25 has been exemplified, but an ROI image obtained by cutting out a part of the region of interest ROI may be included in a search request for a similar case instead of the entire image of the target image 20T. In this case, the region information 25 is not required to be included in the search request for a similar case. As mentioned above, the target image 20T included in a search request for a similar case may be the entire image, and may be an image obtained by cutting out a part of the target image 20T.

Extraction of a target lesion (reference lesion or an extracted lesion), specifying of the type thereof, and calculation of the feature amount ZT may be performed by apparatuses other than the diagnosis support server 17, and the diagnosis support server 17 may only acquire an extraction result and the feature amount ZT of a target lesion.

An output aspect of the reliability information 91 is not limited to the information display screen 90 exemplified in the embodiments, and includes printing output to a paper medium or file output using an electronic mail.

In the above-described embodiments, a hardware structure of processing units performing various processes, such as the evaluation request reception portion 75, the second image analysis portion 76, the information management portion 77, the comparison portion 78, and the screen output control portion 80 of the diagnosis support function unit 61 is, for example, the CPU 47 as a general purpose processor which functions as various processing units by executing software (operation program 55) as described above.

The following various processors may be used instead of all or some of the functions realized by the CPU 47. The various processors include, for example, a programmable logic device (PLD) whose configuration can be changed after being manufactured, such as a field programmable gate array (FPGA), and a dedicated electrical circuit as a processor having a circuit configuration which is exclusively designed to perform specific processes, such as an application specific integrated circuit (ASIC). A hardware structure of such various processors is, more specifically, an electrical circuitry in which circuit elements such as semiconductor elements are combined with each other.

From the above description, the invention design the following appendix can be understood.

APPENDIX 1

A diagnosis support apparatus including:

a reception processor that receives entry of a disease name specified by a doctor visually recognizing a target image which is an examination image of a certain patient and is an image reading target of the doctor;

a type acquisition processor that acquires the type of extracted lesion which is a lesion present in the target image and is extracted by performing image analysis on the target image;

an information management processor that manages registered lesion information in which the disease name and a registered lesion corresponding to the disease name are registered, and reads the registered lesion corresponding to the disease name received by the reception processor;

a comparison processor that compares the type of registered lesion read by the information management processor with the type of extracted lesion acquired by the type acquisition processor; and an output control processor that outputs reliability information regarding the reliability of the disease name received by the reception processor on the basis of a comparison result in the comparison processor.

The above-described various embodiments or various modification examples may be combined with each other as appropriate. In addition to a program, a storage medium storing the program also falls within the scope of the present invention.

EXPLANATION OF REFERENCES

2: medical information system
10: medical care department
11: examination department
12: medical care department terminal
13: modality
14: order management terminal
15: examination image database (DB) server
16: case database (DB) server 17: diagnosis support server (diagnosis support apparatus, similar case search apparatus)
18: network
19: diagnosis support system
20: examination image
20C: case image
20T: target image
21: examination image database (DB)
22: case
23: case database (DB)
25: region information
30, 125: image reading screen
31, 126: image display region
32: similar case display region
33: report creation region
34, 40, 41: entry box
35: search button
36: cursor
37: region designation button
38: designation clear button
39: similar case search button
42: fixed preservation button
43: temporary preservation button
45: storage device
46: memory
47: CPU
48: communication unit
49: data bus
55: operation program
56, 120: registered lesion information
60: similar case search function unit
61: diagnosis support function unit
65: search request reception portion
66: case acquisition portion
67: first image analysis portion
68: feature amount calculation portion
69: similarity calculation portion
70: search portion
75: evaluation request reception portion (reception unit)
76: second image analysis portion (type acquisition unit)
77: information management portion
78: comparison portion
79: similar case acquisition portion
80: screen output control portion (output control unit)
85: scroll bar
90, 90A to 90C: information display screen
91: reliability information
92: OK button
93: back button
94: link
100: frame
101: annotation
105: selection button
110: updated registered lesion information
111, 115, 116: table
127: text information
128: copy button
129: legend
ROI: region of interest
DR: doctor
SA1 to SA14, SB10 to SB17, SC10 to SC16, SD10 to SD14: steps

What is claimed is:

1. A diagnosis support apparatus comprising:
a reception unit that receives entry of a disease name specified by a doctor visually recognizing a target image which is an examination image of a certain patient and is an image reading target of the doctor;
a type acquisition unit that acquires the type of extracted lesion which is a lesion present in the target image and is extracted by performing image analysis on the target image;
an information management unit that manages registered lesion information in which the disease name and a registered lesion corresponding to the disease name are registered, and reads the registered lesion corresponding to the disease name received by the reception unit;
a comparison unit that compares the type of registered lesion read by the information management unit with the type of extracted lesion acquired by the type acquisition unit; and
an output control unit that outputs reliability information regarding the reliability of the disease name received by the reception unit on the basis of a comparison result in the comparison unit.

2. The diagnosis support apparatus according to claim 1, wherein, in a case where there is a non-reference lesion which is a type of lesion included in the extracted lesion and not included in the registered lesion, the output control unit outputs a warning indicating that the non-reference lesion is not referred to in specifying the disease name as the reliability information.

3. The diagnosis support apparatus according to claim 1, further comprising:
a similar case acquisition unit that acquires similar cases from a similar case search apparatus which searches for the similar cases including a case image similar to the target image among a plurality of cases including the case image which is the examination image obtained in the past.

4. The diagnosis support apparatus according to claim 3, wherein the case includes the disease name,
wherein the similar case acquisition unit outputs the similar cases to the output control unit,
wherein the output control unit outputs a similar case selection screen for receiving selection of one of the similar cases, and
wherein the reception unit receives the disease name included in the similar case selected on the similar case selection screen as the disease name specified by the doctor.

5. The diagnosis support apparatus according to claim 3, wherein the case includes the disease name and the type of case lesion which is a lesion presented in the case image,
wherein the similar case acquisition unit outputs the similar cases to the information management unit,
wherein the information management unit updates the registered lesion information on the basis of the disease name included in the similar case from similar case acquisition unit and the type of case lesion, and
wherein the comparison unit compares the type of registered lesion read by the information management unit from the registered lesion information after being updated with the type of extracted lesion acquired from the type acquisition unit.

6. The diagnosis support apparatus according to claim 1, wherein an occurrence frequency of the registered lesion is registered in the registered lesion information for each disease name, and
wherein the output control unit makes output aspects of the reliability information different from each other depending on the occurrence frequency of a non-reference lesion which is a type of lesion included in the extracted lesion and not included in the registered lesion.

7. The diagnosis support apparatus according to claim 1, wherein the output control unit outputs an information display screen on which the reliability information is displayed, and wherein the information display screen is provided with a link for displaying the target image in which a non-reference lesion which is a type of lesion included in the extracted lesion and not included in the registered lesion is present.

8. The diagnosis support apparatus according to claim 7, wherein the output control unit outputs an image display screen on which the target image including the non-reference lesion is displayed in response to selection of the link, and wherein the non-reference lesion and other lesions are displayed in different aspects on the image display screen.

9. An operation method for a diagnosis support apparatus, comprising:

a reception step of receiving entry of a disease name specified by a doctor visually recognizing a target image which is an examination image of a certain patient and is an image reading target of the doctor;

a type acquisition step of acquiring the type of extracted lesion which is a lesion present in the target image and is extracted by performing image analysis on the target image;

an information management step of managing registered lesion information in which the disease name and a registered lesion corresponding to the disease name are registered, and reads the registered lesion corresponding to the disease name received in the reception step;

a comparison step of comparing the type of registered lesion read in the information management step with the type of extracted lesion acquired in the type acquisition step; and an output control step of outputting reliability information regarding the reliability of the disease name received in the reception step on the basis of a comparison result in the comparison step.

10. A diagnosis support system including a diagnosis support apparatus supporting a doctor's diagnosis and a client terminal connected to the diagnosis support apparatus via a network and operated by the doctor, the system comprising:

a reception unit that receives entry of a disease name specified by the doctor visually recognizing a target image which is an examination image of a certain patient and is an image reading target of the doctor;

a type acquisition unit that acquires the type of extracted lesion which is a lesion present in the target image and is extracted by performing image analysis on the target image;

an information management unit that manages registered lesion information in which the disease name and a registered lesion corresponding to the disease name are registered, and reads the registered lesion corresponding to the disease name received by the reception unit;

a comparison unit that compares the type of registered lesion read by the information management unit with the type of extracted lesion acquired by the type acquisition unit; and an output control unit that outputs reliability information regarding the reliability of the disease name received by the reception unit on the basis of a comparison result in the comparison unit.

* * * * *